(12) United States Patent
Qin et al.

(10) Patent No.: US 12,285,328 B2
(45) Date of Patent: Apr. 29, 2025

(54) SOFT TISSUE SUPPORTS, AND METHODS OF MAKING AND USING SAME

(71) Applicant: LifeNet Health, Virginia Beach, VA (US)

(72) Inventors: Xiaofei Qin, Virginia Beach, VA (US); Michael LaPrade, Virginia Beach, VA (US); Jingsong Chen, Virginia Beach, VA (US); Joshua Jones, Virginia Beach, VA (US); Austin Johnson, Virginia Beach, VA (US); Erich Lohmann, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 751 days.

(21) Appl. No.: 17/440,522

(22) PCT Filed: Mar. 20, 2020

(86) PCT No.: PCT/US2020/023921
§ 371 (c)(1),
(2) Date: Sep. 17, 2021

(87) PCT Pub. No.: WO2020/191320
PCT Pub. Date: Sep. 24, 2020

(65) Prior Publication Data
US 2022/0151765 A1     May 19, 2022

Related U.S. Application Data

(60) Provisional application No. 62/970,965, filed on Feb. 6, 2020, provisional application No. 62/821,325, filed on Mar. 20, 2019.

(51) Int. Cl.
*A61F 2/12*     (2006.01)

(52) U.S. Cl.
CPC ........ *A61F 2/12* (2013.01); *A61F 2230/0008* (2013.01); *A61F 2230/0071* (2013.01); *A61F 2240/004* (2013.01); *A61F 2250/0015* (2013.01)

(58) Field of Classification Search
CPC ................ A61F 2/12; A61F 2230/0008; A61F 2230/0071; A61F 2240/004; A61F 2250/0015
See application file for complete search history.

(56) References Cited

U.S. PATENT DOCUMENTS

| 5,759,204 A | 6/1998 | Seare |
| 6,293,970 B1 | 9/2001 | Wolfinbarger et al. |

(Continued)

FOREIGN PATENT DOCUMENTS

| WO | 2014130953 A1 | 8/2014 |
| WO | 2017066568 A1 | 4/2017 |

OTHER PUBLICATIONS

Extended European Search Report for European Application No. 20774114.1, dated Nov. 18, 2022, 7 pages.

(Continued)

*Primary Examiner* — Suzette J Gherbi
(74) *Attorney, Agent, or Firm* — Matney Legal Group PLLC

(57) ABSTRACT

Soft tissue supports, soft tissue implants, and methods of making and using soft tissue supports are disclosed. One soft tissue support includes a unitary piece of processed porous tissue material having an anterior portion and a posterior portion. The anterior and posterior portions define a cavity therebetween. The cavity is sized to receive a breast implant therein. The cavity has at least one opening sized to receive the breast implant therethrough. One soft tissue implant includes the soft tissue support and a breast implant positioned within the cavity of the soft tissue support. The (Continued)

implant may further include a soft tissue graft configured to support the processed porous tissue material and the breast implant. A method of using a soft tissue support includes inserting a breast implant into the soft tissue support, and implanting the soft tissue support containing the breast implant in the cavity.

80 Claims, 23 Drawing Sheets

(56) References Cited

U.S. PATENT DOCUMENTS

| | | | |
|---|---|---|---|
| 6,544,289 B2 | 4/2003 | Wolfinbarger et al. | |
| 6,569,200 B2 | 5/2003 | Wolfinbarger et al. | |
| 6,734,018 B2 | 5/2004 | Wolfinbarger et al. | |
| 6,743,574 B1 | 6/2004 | Wolfinbarger et al. | |
| 7,063,726 B2 | 6/2006 | Crouch et al. | |
| 7,338,757 B2 | 3/2008 | Wolfinbarger et al. | |
| 7,476,249 B2 | 1/2009 | Frank | |
| 8,563,232 B2 | 10/2013 | Wolfinbarger et al. | |
| 8,574,826 B2 | 11/2013 | Wolfinbarger et al. | |
| 10,532,127 B2 | 1/2020 | Limen et al. | |
| 11,434,469 B2 * | 9/2022 | Qin | A61F 2/02 |
| 2005/0142162 A1 * | 6/2005 | Hunter | A61L 31/16 |
| | | | 424/423 |
| 2006/0030939 A1 * | 2/2006 | Frank | A61F 2/12 |
| | | | 623/8 |
| 2007/0088434 A1 * | 4/2007 | Frank | A61F 2/12 |
| | | | 623/8 |
| 2007/0196421 A1 * | 8/2007 | Hunter | A61K 31/496 |
| | | | 623/23.72 |
| 2009/0082864 A1 * | 3/2009 | Chen | A61F 2/12 |
| | | | 623/8 |
| 2009/0312746 A1 * | 12/2009 | Khouri | A61F 2/12 |
| | | | 604/522 |
| 2010/0030340 A1 | 2/2010 | Wolfinbarger et al. | |
| 2011/0009960 A1 * | 1/2011 | Altman | A61F 2/12 |
| | | | 623/8 |
| 2011/0015757 A1 | 1/2011 | Wolfinbarger et al. | |
| 2011/0022171 A1 * | 1/2011 | Richter | A61L 27/3633 |
| | | | 623/8 |
| 2011/0054604 A1 * | 3/2011 | Becker | A61F 2/12 |
| | | | 623/8 |
| 2011/0054605 A1 * | 3/2011 | Becker | A61F 2/12 |
| | | | 623/8 |
| 2012/0004723 A1 * | 1/2012 | Mortarino | A61F 2/12 |
| | | | 623/8 |
| 2012/0053690 A1 * | 3/2012 | Frank | A61F 2/12 |
| | | | 623/8 |
| 2013/0218294 A1 | 8/2013 | Wolfinbarger et al. | |
| 2013/0253645 A1 * | 9/2013 | Kerr | A61F 2/12 |
| | | | 623/8 |
| 2013/0280319 A1 * | 10/2013 | Mathiowitz | A61L 17/005 |
| | | | 514/180 |
| 2014/0065238 A1 | 3/2014 | Wolfinbarger et al. | |
| 2014/0154663 A1 | 6/2014 | Wolfinbarger et al. | |
| 2014/0180437 A1 | 6/2014 | Wolfinbarger et al. | |
| 2014/0257517 A1 | 9/2014 | Deichmann et al. | |
| 2017/0367807 A1 * | 12/2017 | Chen | A61L 27/3691 |
| 2018/0008745 A1 * | 1/2018 | Park | A61L 27/60 |
| 2018/0028720 A1 * | 2/2018 | De Groot-Barrere | A61L 27/50 |
| 2018/0044629 A1 * | 2/2018 | Qin | A61L 27/56 |
| 2019/0254807 A1 * | 8/2019 | Limem | A61K 35/35 |
| 2022/0372438 A1 * | 11/2022 | Qin | C12N 5/0068 |
| 2023/0108501 A1 * | 4/2023 | Weiss | A61L 27/58 |
| | | | 424/423 |

OTHER PUBLICATIONS

International Preliminary Report on Patentability for International Application No. PCT/US2020/023921, dated Sep. 16, 2021, 11 pages.

International Search Report and Written Opinion for International Application No. PCT/US2020/023921, dated Jul. 27, 2020, 13 pages.

* cited by examiner

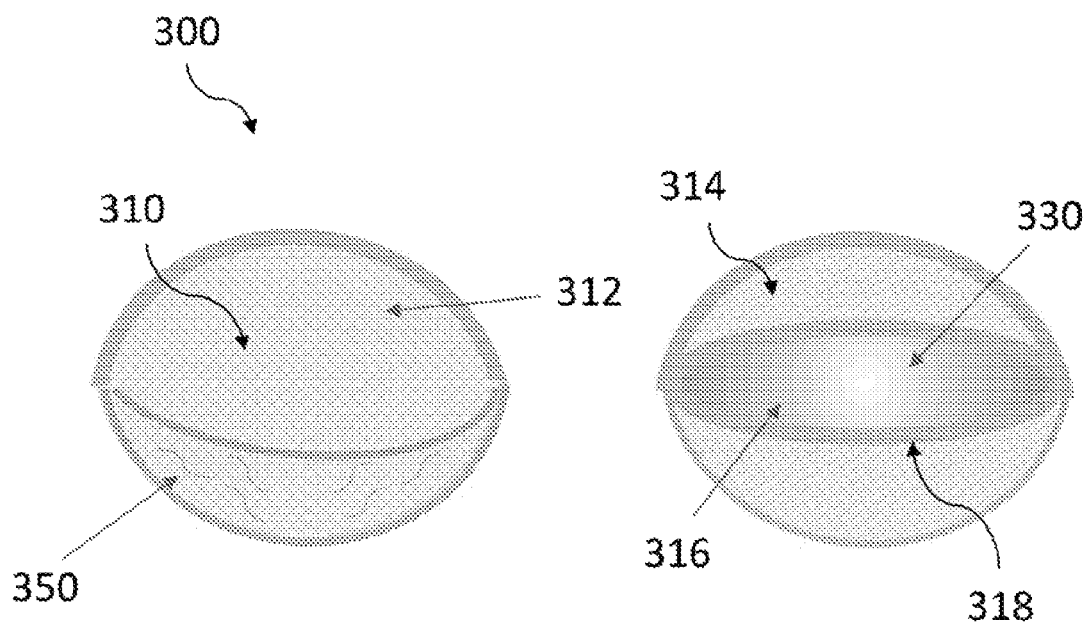
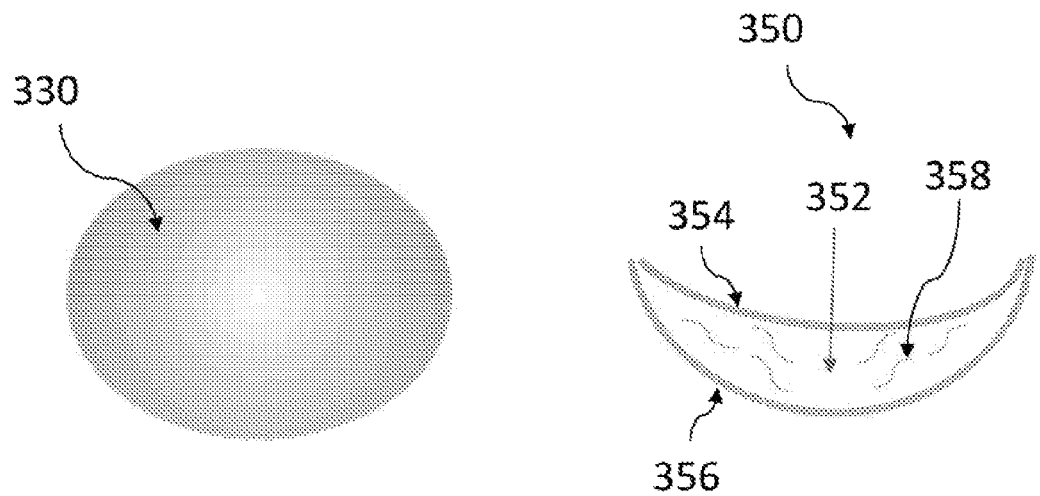
FIG. 4A  FIG. 4B
FIG. 4C  FIG. 4D

SOFT TISSUE SUPPORTS, AND METHODS OF MAKING AND USING SAME

This Application is the U.S. National Phase Application of PCT International Application No. PCT/US2020/023921, filed Mar. 20, 2020, entitled SOFT TISSUE SUPPORTS, AND METHODS OF MAKING AND USING SAME, which claims priority of U.S. Provisional Application No. 62/821,325, filed on 20 Mar. 2019, entitled SOFT TISSUE SUPPORTS, AND METHODS OF MAKING AND USING SAME, and of U.S. Provisional Application No. 62/970,965 filed on 6 Feb. 2020, entitled SOFT TISSUE SUPPORTS, AND METHODS OF MAKING AND USING SAME the contents of which are incorporated herein by reference in their entirety for all purposes. The present invention relates to soft tissue supports, soft tissue implants incorporating soft tissue supports, methods of preparing soft tissue supports, and methods of use thereof. The present invention also relates to soft tissue supports for use in mastopexy or breast reconstruction procedures.

TECHNICAL FIELD

Background

A wide variety of soft tissue products are used in medical, surgical, veterinary, and other applications. These soft tissue products can be used in load-bearing and non-load bearing applications and can be supplied in a variety of forms. The intended use of the soft tissue product may dictate certain aspects of its form such as size, shape, or thickness. General soft tissue materials, however, may be unable to meet desired dimensions, or may require substantial modification before they are suitable for a particular use.

SUMMARY

Soft tissue supports, soft tissue implants, and methods of making and using soft tissue supports are disclosed.

In one example, a soft tissue support is disclosed. The soft tissue support includes a unitary piece of processed porous tissue material having an anterior portion and a posterior portion. The anterior and posterior portions define a cavity therebetween. The cavity is sized to receive a breast implant therein. The cavity has at least one opening sized to receive the breast implant therethrough.

In another example, a soft tissue implant is disclosed. The soft tissue implant includes a soft tissue support, which may take the form of a unitary piece of processed porous tissue material having an anterior portion and a posterior portion. The anterior and posterior portions define a cavity therebetween. The cavity has an opening. The soft tissue implant further includes a breast implant positioned within the cavity. The soft tissue implant may further include a soft tissue graft configured to support the processed porous tissue material and the breast implant.

In another example, a method of using a soft tissue support is disclosed. The method includes inserting a breast implant into a unitary piece of processed porous tissue material, and implanting the unitary piece of processed porous tissue material containing the breast implant in the cavity. The method may further include supporting the unitary piece of processed porous tissue material containing the breast implant with a soft tissue graft.

In another example, a method of making a soft tissue support is disclosed. The method includes dispersing one or more soft tissues to produce a dispersed soft tissue material, molding the dispersed soft tissue material into a predetermined shape for the soft tissue support, and setting the molded dispersed soft tissue material in the predetermined shape to produce the soft tissue support.

In another example, another soft tissue implant is disclosed. The soft tissue implant includes a unitary piece of processed porous tissue material defining a cavity sized to receive a breast implant therein. The soft tissue implant further includes a soft tissue graft configured to support the processed porous tissue. The soft tissue graft is meshed to form a plurality of apertures in the soft tissue graft.

In another example, a method of using a soft tissue implant is disclosed. The method includes inserting a breast implant into a cavity defined within a unitary piece of processed porous tissue material, the processed porous tissue material supported by a scaffold, the scaffold being a meshed soft tissue graft or a synthetic mesh material, and implanting the scaffold and the unitary piece of processed porous tissue material containing the breast implant in the cavity.

In another example, a method of making a soft tissue implant is disclosed. The method includes dispersing one or more soft tissues to produce a dispersed soft tissue material, positioning a scaffold and the dispersed soft tissue material in a mold, the scaffold being a meshed soft tissue graft or a synthetic mesh material, molding the dispersed soft tissue material with the scaffold into a predetermined shape for the soft tissue implant, and setting the molded dispersed soft tissue material with the scaffold in the predetermined shape to produce the soft tissue implant.

In another example, another soft tissue implant is disclosed. The soft tissue implant includes a first unitary piece of processed porous tissue material having at least one first mating structure, and a second unitary piece of processed porous tissue material having at least one second mating structure configured to mate with respective ones of the at least one first mating structure of the first unitary piece of processed porous tissue material.

In another example, a mold for making a soft tissue implant is disclosed. The mold includes an outer mold section configured to define an outer mold surface for molding an outer surface of the soft tissue implant, and an inner mold section configured to define an inner mold surface for molding an inner surface of the soft tissue implant. The outer mold section and the inner mold section together define a mold volume for molding the soft tissue implant. The mold volume at least partially surrounds the inner mold section. The inner mold section is removable from the mold volume following molding and setting of the soft tissue implant.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 4A-4D show an example of a soft tissue implant incorporating the soft tissue support of FIGS. 1A-1C.

FIGS. 20A and 20B show examples of a mold for manufacturing a soft tissue implant.

DETAILED DESCRIPTION

Figure 1A:
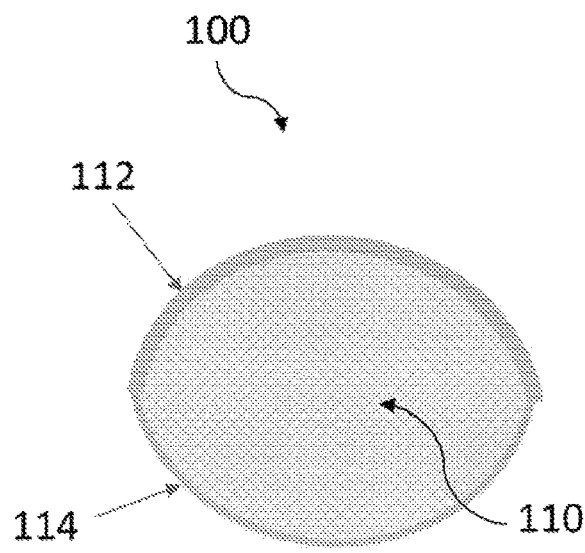
FIGS. 1A-1C show front, rear, and cross-sectional side views of an example of a soft tissue support.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The detailed description below and the accompanying drawings disclose examples of soft tissue supports and implants, and methods of making and using soft tissue supports and implants. As referred to herein, soft tissue implants refer to materials and/or combinations of materials designed for implantation in the human body and including one or more soft tissue components. Such soft tissue implants may include additional, non-soft tissue components or implants, including synthetic components such as conventional synthetic breast implants, pacemakers, and/or synthetic or composite mesh structures, as discussed in greater detail below. The examples of soft tissue supports and implants have sizes, shapes, and thicknesses selected for particular uses.

The examples discussed below may be particularly suitable for use in mastopexy or breast reconstruction procedures. Mastopexy, or breast lift, is a procedure designed to improve the appearance of sagging or ptotic breasts. For example, one goal of the surgery is to improve the shape and position of the breast while minimizing visible scars. Breast reconstruction is a procedure used to restore form and function after mastectomy. The goals of implant-based breast reconstruction include: recreation of the breast mound—including defining the contour of the lower pole to reestablish normal ptosis and the creation of aesthetically pleasing inframammary fold. Various procedures and modifications of mastopexy are known in the art.

The subject matter of this disclosure is not limited to mastopexy, lumpectomy, or breast reconstruction procedures. Other potential uses of the disclosed soft tissue supports and implants include, for example, use in wound repair, dental procedures, shoulder and/or rotator cuff repair and reconstruction, sports medicine procedures, hernia treatment procedures, joint repair and/or reconstruction, minimally invasive surgeries, and/or in plastic or cosmetic procedures. The disclosed soft tissue can further be used as carrier for cells or host tissue. Other potential applications for the disclosed soft tissue supports and/or implants will be apparent from the disclosure.

Examples discussed below and shown in the drawings improve over the art by providing a suitable size, shape, and thickness for a predetermined procedure, thereby eliminating the need for substantial processing or cutting of the soft tissue prior to implantation. Suitable shapes for the soft tissue supports and implants described herein may include curved or straight edges. Suitable shapes may include circular, elliptical, rectangular, square, triangular, elongated, or other shapes. Soft tissue supports may be shaped as regular or irregular polygons.

The examples discussed below may include porous soft tissue which has been processed in a manner to promote angiogenesis (formation of blood vessels) and tissue ingrowth following implantation, thereby speeding the post-implantation healing process. The porous soft tissue has a desired pore size and structure to support cell infiltration following implantation. Cells infiltrate quickly and initiate angiogenesis and remodeling and the tissue retains the majority of its volume during the remodeling process. The porous soft tissue can be molded or fabricated to any desired thickness, size, and two- or three-dimensional shape to meet the needs of the surgical site. The disclosed porous soft tissue can be compressed and will regain its original size and shape after releasing the compression and/or rehydration. Using compressed soft tissue enables delivery to surgical sites with minimally invasive surgery. The porous soft tissue may be stiff but compressible, and thereby improve handling and simplify laying out across recipient tissue relative to conventional sheets of dermis that tend to fold over easily. The porous soft tissue can be used to fill volumes and provide cushioning, and can be positioned when wet or dry and rehydrated at the surgical site. The porous soft tissue may incorporate a scaffold, such as meshed soft tissue or synthetic mesh material, to add biomechanical and suture retention strength and durability.

While the following examples are described chiefly with respect to particular procedures (such as mastopexy or breast reconstruction), it should be readily apparent that the examples herein are not so limited. The following examples and variations thereof may alternatively be used in any number of procedures requiring the use of a soft tissue implants. Other suitable procedures will be apparent from the description herein.

Definitions are set forth below to provide a clear and consistent understanding of the specification and claims, including the scope to be given such terms.

About. The term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

And/or. The use of "and/or" is defined inclusively such that the term "a, b and/or c" should be read to include all the combination of a, b, and c, including "a, b, and c," "a and b," "a and c," "b and c," "a, b, or c," "a or b," "a or c," "b or c," "a," "b," and "c." hole Aperture. The term "aperture" as used herein is intended to encompass any separation in a surface of the soft tissue, including holes, slits, cavities, voids, fenestrations, channels, or other types of openings, regardless of whether that separation extends part of the way or all of the way through the soft tissue.

Biocompatible. The term "biocompatible" as used herein is intended to encompass any material which does not provoke an adverse response in a patient. For example, a suitable biocompatible material when introduced into a patient does not itself provoke a significant immune response, and is not toxic to the patient.

Biomechanical strength. The term "biomechanical strength" as used herein is intended to encompass those properties exhibited by tissue, including loading strength, compressive strength, tensile strength, and suture retention strength.

Impregnating. The term "impregnating" as used herein is intended to encompass any processing conditions which result in filling the internal matrix of tissue with an identified material.

Internal matrix. The term "internal matrix" as used herein is intended to encompass the intercellular substance of such soft tissue including for example ligaments and tendons, including collagen and elastin fibers and base matrix substances.

Plasticizer. The term "plasticizer" as used herein is intended to encompass any biocompatible compounds which can easily displace/replace water at the molecular level and preferably have a low molecular weight such that the plasticizer fits into the spaces available to water within the molecular structure of the bone or soft tissue. Such plasticizers are preferably not toxic to the cellular elements of tissue into which the tissue is to be placed. Suitable plasticizers are described in U.S. Pat. No. 6,569,200, the contents of which are incorporated herein by reference in their entirety.

Porous tissue material. The term "porous tissue material" as used herein is intended to encompass a three-dimensional tissue structure that is porous, elastic, flexible, fibrous, and resilient. In addition, the preferred "porous tissue material" is substantially unitary, coherent, and/or cohesive in the sense of holding together in a single piece and/or staying substantially intact. As used herein, the terms "coherent" or "cohesive" refer to the property that the elements of the tissue structure are maintained substantially intact (in the sense of holding together in a unitary structure rather than becoming disassembled or separated). In a dry state, the porous tissue material may quickly absorb fluid. In the wet state, the porous tissue material may maintain the porosity, cohesiveness, and/or integrity. The wet porous structure may resist certain external stress or strain, and bounce back and reabsorb fluid after being released from external stress or strain.

Processed tissue material. The term "processed tissue material" as used herein is intended to encompass native, normal tissue that has been procured from an animal source (e.g. human or non-human, such as bovine, porcine, canine including, but not limited to, a dog, equine, ovine, or non-human primate including, but not limited to, ape and gorilla, in origin), preferably a mammal, and mechanically cleaned of attendant tissues and/or chemically cleaned of cells and cellular debris.

Soft tissue graft. The term "soft tissue graft" as used herein is intended to encompass load-bearing and non-load-bearing processed tissue material composed of an internal matrix which includes collagen, elastin, and high molecular weight solutes which during cleaning may be removed.

The soft tissue supports disclosed herein may be derived from allogenic, autogenic, or xenogenic sources. The tissue material used for the supports may be processed from human or animal tissue. In one aspect, processed tissue material used for the support may be derived from native tissues, such as stomach, intestine, dermis, fascia lata, pericardium, bladder, and dura mater. The processed tissue material may be, for example, biologically-derived collagenous materials. When implanted into a mammalian patient, the processed tissue material may undergo controlled biodegradation occurring with adequate living cell replacement such that the original implanted tissue is remodeled by the patient's living cells, and, in some examples, the tissue does not interfere with radiographic imaging. Examples of additional types of fascia that may be used include: fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. Connective tissues may be obtained from vertebrates. Connective tissues may also be the product of biotechnological methods, for example, tissue engineered connective tissues produced using cell culture methods, and such a product of biotechnological methods may be included as the soft tissue described herein. In some embodiments, the soft tissues herein may have human, non-human animal, bovine, equine, porcine, ovine, caprine, or piscine origins, among others.

Specific examples of connective tissues that may be used include but are not limited by at least, fascia, dermis, tendons, ligaments, pericardium, urethra, small intestine, muscle, or skin. Examples of different types of fascia that may be used include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others.

The soft tissue supports described herein may be manufactured by dispersing one or more soft tissue material(s) at a temperature between about 0-50° C. to produce a dispersed soft tissue material which forms the body of the soft tissue support. The dispersing may include loosening the network of extracellular materials in the soft tissue. In some embodiments, the dispersed soft tissue described herein may include a network of fibers. Compared to the native soft tissues, the dispersed soft tissues may have more space among (and/or in between) the extracellular materials and an increased void volume, and the fibers or fiber bundles may be randomly interwoven or intertwined by the dispersion process The native soft tissue is a tissue that connects, supports, and/or surrounds other body structures. In some embodiments, the native soft tissue may be selected from a part or whole organ, (e.g. liver, kidney, pancreases, heart, spleen, and lung), muscle, fat, blood vessel, nerve, tendon, ligament, lining of joints, skin, dermis, pericardium, endocardium, mucosal tissue, fascia, arteries or veins, dura mata, periosteum, amniotic membrane, placental membrane, chorionic membrane, umbilical cord, bladder, small or large intestine, urethra, and/or placenta.

The dispersed soft tissue described herein may or may not optionally include "crudely fragmented connective tissue," referring to connective tissue that has been sliced, ground, carved, chipped, chopped, minced, cut, dissected, rent, ripped, sectioned, snipped, diced, shaved, comminuted, or trimmed into fragments. Such fragmented connective tissue may have an average diameter greater than about 50 microns and less than about 0.5 cm, for example, having cut dimensions of approximately 0.5×0.5 cm, and a thickness appropriate to the tissue being crudely fragmented. In some embodiments, the crude fragments may not be of uniform size. In one aspect, the dispersed soft tissue described herein may or may not include "homogenized connective tissue" or "connective tissue homogenate" containing connective tissue that has been reduced to particles that are uniformly small and evenly distributed. Homogenized connective tissue may optionally include at least one of water, aqueous solutions, or water miscible polar organic solvents, in addition to the particles. The homogenized connective tissues used include particles having an average diameter of less than about 50 microns. In some embodiments, the homogenized connective tissue may be prepared by shear-induced shredding of a composition comprising connective tissue, and optionally, at least one of water, an aqueous solution and a water miscible polar organic solvent.

In another aspect, the dispersed soft tissue and/or implant may include one, two, three, four, five, six, seven, eight or more soft tissues described herein. For example, the dispersed soft tissue and/or implant may be principally comprised of or consist of or include (i) dermis or fascia and/or (ii) placental tissues, adipose tissues, tendon ligament tissues, or nerve tissue, or may comprise a combination of any of the preceding, or may specifically exclude any of the preceding. In some embodiments, the weight ratio of (i) dermis or fascia to (ii) placental tissues, adipose tissues, tendon ligament tissues, or nerve tissue is about 0.1, 0.2, 0.3, 0.4, 0.5, 0.6, 0.7, 0.8, 0.9, 1, 2, 3, 4, 5, 6, 7, 8, 9 or 10. For another example, the dispersed soft tissue and/or implant may include a combination of (i) amniotic membrane and (ii) chorionic membrane. In some embodiments, the weight ratio of (i) amniotic membrane to (ii) chorionic membrane is about 0.1, 0.2, 0.3, 0.4, 0.5, 0.6, 0.7, 0.8, 0.9, 1, 2, 3, 4, 5, 6, 7, 8, 9 or 10, with a preferred weight ratio range of 0.1-10, more preferably a range of 0.5-5, or more preferably a range of 0.7-3. In some embodiments, the different types of soft tissue may be layered, for example, a layer of dispersed soft tissue made with amniotic membrane on top of a layer of dispersed soft tissue made with chorionic membrane, or a layer of dispersed soft tissue made with chorionic membrane sandwiched in two layers of dispersed soft tissue made with amniotic membrane. In other embodiments, the dispersed soft tissue and/or implant may include a combination of soft tissues from different sources, such as human, non-human animal, bovine, equine, porcine, ovine, caprine, or piscine origins, among others.

The method described herein may include adding one or more additional soft tissue to the dispersed soft tissue and/or implant described herein. Such an added step (of adding one or more additional soft tissue) may be performed before or after dispersing the additional soft tissue.

In another aspect, the soft tissue may be dispersed at a temperature above about −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36 or 37° C. In some embodiments, the soft tissue may be dispersed at a temperature below about −70, −60, −50, −40, −30, −20, −10, −5, 0, 5, 10, 15, 16, 17, 18, 19, 20, 21, 22, 23, 24, 25, 26, 27, 28, 29, 30, 31, 32, 34, 35, 36, 37, 38 or 39° C. In additional embodiments, the soft tissue may be dispersed at a temperature of about −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36, or 37° C. In further embodiments, the soft tissue may be dispersed at a temperature between about −80 and about 50° C., −20 and about 50° C., −10 and about 50° C., about −5 and about 50° C., about 0 and about 50° C., about 0 and about 37° C., about 5 and about 24° C., about 10 and about 24° C., about 15 and about 24° C., about −5 and about 10° C., about −5 and about 15° C., or about 0 and about 15° C. In another aspect, the soft tissue may be dispersed mechanically by chopping, skiving, milling, grinding, slicing and/or beating the soft tissue (e.g. by a blender, a beater, and a mixer). In some embodiments, the temperature of the soft tissue may rise above ambient temperature due to the dispersing process, but no additional heat is applied to the soft tissue. In a preferred embodiment, the temperature of soft tissue may be controlled by adding, e.g., cold solution (e.g., water and saline) or ice (e.g., made from water or isotonic solution) to the soft tissue prior to, or during, the dispersing process. In another embodiment, the method may exclude treating the soft tissue with heat above about 24, 25, 26, 27, 28, 29, 30, 31, 32, 33, 35, 36, 37, 38, 40, 45, 50, 60, 70, 80, 90, 100, 150, or 200° C. prior to, during and/or after the dispersing. In some embodiments, the method excludes treating the soft tissue with heat below about 50, 70, 90, or 110° C. prior to, during, and/or after the dispersing. In other embodiments, the method excludes treating the soft tissue with heat between about 26 and about 200° C., about 30 and about 150° C., about 40 and about 120° C., about 50 and about 110° C., and about 50 and about 100° C. prior to, during, and/or after the dispersing. In another aspect, the method may exclude sonication, microwave irradiation, or conventional heat transfer from a heating component, among other methods known in the art.

In some embodiments, the one or more soft tissue(s) described herein is dispersed for about 5 seconds, 10 seconds, 15 seconds, 20 seconds, 25 seconds, 30 seconds, 40 seconds, 50 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or more. In additional embodiments, the one or more soft tissue(s) described herein is dispersed for about 20 seconds, 30 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or less. In further embodiments, the one or more soft tissue(s) described herein is dispersed for between about 20 seconds and 72 hours, about 30 seconds and 30 minutes, about 30 seconds and 20 minutes, about 30 seconds and 10 minutes, preferably between about 1 minute and 20 minutes, between about 1 minute to 10 minutes, or between about 1 minute to 6 minutes.

In some embodiments, the one or more soft tissue(s) is dispersed in the presence of a solution or solvent (e.g. water, and saline solution). The solution or solvent may be in the form of liquid or solid. In additional embodiments, the one or more soft tissue(s) is dispersed in the presence of a solid (e.g. ice formed from water, and solid formed from saline solution). The solid may comprise one or more salt granulate and/or one or more sugar granulate. The salt granulate may for example comprise NaCl2 and/or CaCl2, and the sugar granulate may for example comprise glucose, sucrose, and/or fructose. In another embodiment, the solid may have the size of about 0.5 mm3, 1 mm3, 2 mm3, 4 mm3, 10 mm3, 2 cm3, 4 cm3, 6 cm3, 8 cm3, 10 cm3, or above. In additional embodiments, the size of a solid may be between about 0.5 mm3 and 20 cm3, between about 1 mm3 and 20 cm3, between about 5 mm3 and 20 cm3, between about 1 cm3 and 20 cm3, or between about 1 cm3 and 10 cm3. In further embodiments, the method described herein may further comprise dissolving the solid during and/or after dispersing the soft tissue(s). In yet additional embodiments, a weight ratio of the one or more moist soft tissue(s) to solution or solvent in the dispersed soft tissue (in other words, the wet weight of tissue to the solution) is about 0.01, 0.05, 0.1, 0.2, 0.3, 0.4, 0.5, 0.6, 0.7, 0.8, 0.9 or 1.0 or more. The weight ratio of the dispersed one or more soft tissue(s) to solution or solvent in the dispersed soft tissue may also be about 0.02, 0.05, 0.1, 0.2, 0.3, 0.4, 0.5, 0.6, 0.7, 0.8, 0.9 or 1.0 or less. Further, the weight ratio of one or more soft tissue(s) to solution or solvent in the dispersed soft tissue may be from about 0.010 to 10.0, preferably from about 0.02 to 2.0, more preferably from about 0.04 to 1.0, from about 0.05 to 1.5, from about 0.05 to 1.0, or from about 0.1 to 1.0.

In some embodiments, the weight percentage of said one or more soft tissue(s) in said dispersed soft tissue is about 2, 5, 10, 15, 20, 30, 40, 50, 60, 70, 80, 90, 92, 94, 96, 98, 100% or more in a dry state. In additional embodiments, the weight percentage of said one or more soft tissue(s) in said dispersed soft tissue is about 3, 5, 10, 15, 20, 30, 40, 50, 60, 70, 80, 90, 91, 93, 95, 97, 99, 100% or less in a dry state. In further embodiments, the weight percentage of said one or more soft tissue(s) in said dispersed soft tissue is from about 2% to about 100%, preferably from about 50% to about 90%, from about 50% to about 80%, from 60% to 100%, from 80% to about 100%, or from about 60% to about 100% in a dry state.

In some embodiments, the weight percentage of said dispersed soft tissue in the soft tissue support and/or implant is about 50, 60, 70, 80, or 90% or more in a dry state. In additional embodiments, the weight percentage of said dispersed soft tissue in the soft tissue support and/or implant is about 50, 60, 70, 80, or 90%, or 100% or less in a dry state. In further embodiments, the weight percentage of said dispersed soft tissue in the soft tissue support and/or implant is from about 50% to about 100%, from about 70% to about 100%, from about 80% to about 100%, or from about 90% to about 100% in a dry state. The amount of dispersed soft tissue in the soft tissue support and/or implant may be varied to adjust the density, porosity, and/or viscosity characteristics of the soft tissue support and/or implant as well as the re-hydration characteristics of the porous structure. Moreover, incorporating additional dispersed soft tissue in the soft tissue support and/or implant may strengthen the three-dimensional framework and increase the integrity of the porous structure. Incorporating more dispersed soft tissue in the soft tissue support and/or implant also may decrease or increase the cellular response towards the framework of the porous structure by facilitating cellular attachment, migration, and/or proliferation.

In some embodiments, the dispersed soft tissue may be resistant to absorption after implantation. For example, soft tissue supports formed from the dispersed soft tissue may maintain 30-100% of their thickness from the 1st month of implantation through 6 months after implantation; maintain 50-100% of their thickness from the 1st month of implantation through 6 months after implantation; maintain 50-80% of their thickness from the 1st month of implantation through 6 months after implantation; maintain 30-100% of their thickness from the 1st month of implantation through 12 months after implantation; or maintain 50-80% of their thickness from the 1st month of implantation through 12 months after implantation.

In one example, the dispersed soft tissue does not require, and thus in a preferred embodiment does not comprise, an additional crosslinker or carrier in addition to natural (i.e., endogenous) crosslinker(s) and natural carrier(s) from the one or more soft tissue(s). Thus, in a preferred embodiment, the methods and resulting products may consist essentially of (and/or consist of) natural crosslinker(s) and natural carrier(s) from the one or more soft tissue(s). In another embodiment, however, the methods and resulting products may optionally include the addition of additional crosslinker(s) or carrier(s) in addition to the natural crosslinker(s) and natural carrier(s) from the one or more soft tissue(s) after dispersing the soft tissue, and, accordingly, the soft tissue support and/or implant in this embodiment may optionally comprise such additional non-natural crosslinker(s) or carrier(s) as described below.

With regard to naturally occurring crosslinkers and carriers, the soft tissue described herein may comprise a naturally occurring crosslinker that is a physical and/or chemical bond at least between two parts of the soft tissue. The chemical bonds may include ionic, covalent, non-covalent, and/or metallic bonds. Furthermore, as indicated above, in some preferred embodiments, the methods described herein do not include crosslinking the one or more soft tissue(s) and/or the dispersed soft tissue by non-naturally occurring bonds using non-naturally occurring crosslinkers.

With specific regard to non-naturally occurring crosslinkers or carriers, in some embodiments, as indicated above, the dispersed soft tissue described herein may optionally include the addition of a non-naturally occurring crosslinkers, also referred to herein as crosslinking agents, in addition to the natural crosslinker(s) and natural carrier(s) from the one or more soft tissue(s) after dispersing the soft tissue, wherein the optionally added non-naturally occurring crosslinker can be selected from the group consisting of propylene glycol alginate, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC), dimethyl suberimidate (DMS), dimethyl-3-3'-dithiobispropionimidate (DTBP), and acryl azide, and/or combinations thereof. In additional embodiments, the dispersed soft tissue described herein may optionally include a photoactive agent selected from the group consisting of a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis(3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dye, ethyl eosin, and eosin Y, and/or combinations thereof.

In another aspect, the soft tissue described herein may also comprise a natural carrier. The carriers described herein are configured to form a three-dimensional framework to be injected or implanted into wound, defect, and/or surgical sites. The natural carriers are carriers that naturally occur in a soft tissue, and, for example, include extracellular matrices, such as collagen and hyaluronic acid or elastin. In some embodiments, the dispersed soft tissue described herein may optionally include a non-naturally occurring carrier selected from the group consisting of gelatin, agarose, modified hyaluronic acid, propylene glycol alginate, polyethylene glycol, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, and polylactic acid, and/or combinations comprising at least one of the foregoing polymers. In additional potential embodiments, the dispersed soft tissue described herein may optionally include salts of calcium, barium, aluminum, strontium, copper, zinc, magnesium, manganese, cobalt, or iron, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), acryl azide, and/or combinations thereof.

As indicated above, in one example the dispersed soft tissue does not require, and thus in a preferred embodiment does not comprise, an additional crosslinker in addition to a natural crosslinker(s) from the soft tissue. In another embodiment, however, the dispersed soft tissue described herein may optionally include an additional carrier in addition to a natural carrier(s) from the soft tissue. For example, the dispersed soft tissue in an alternative embodiment may optionally comprise, alginate, propylene glycol alginate, native or crosslinked chitosan, starch, polyethylene glycol, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxylpectin, or carrageenan. The dispersed soft tissue may or may not optionally include a carrier solution. If included, the carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The optional carrier solution may also comprise natural and/or synthetic polymers such as native or modified collagen, gelatin, agarose, modified hyaluronic acid, fibrin, chitin, biotin, avidin, MATRIGEL®, HUMAN EXTRACELLULAR MATRIX®, proteoglycans, laminin, fibronectin, elastin, heparin, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers in addition to a natural carrier(s) from the soft tissue. In additional embodiments, for example, the dispersed soft tissue described herein may or may not include an optional additional carrier in addition to a natural carrier(s) from the soft tissue, wherein the carrier is selected from the group consisting of native collagen, hyaluronic acid, fibrin, chitin, biotin, avidin, MATRIGEL®, HUMAN EXTRACELLULAR MATRIX®, proteoglycans, laminin, fibronectin, elastin, heparin, alginate, genipin, chitosan, starch, glucose or ribose, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxyl pectin, and carrageenan, and/or combinations thereof. Moreover, in further embodiments, the dispersed soft tissue described herein may or may not include an optional additional crosslinker in addition to a natural crosslinker(s) from the soft tissue, wherein the optional additional crosslinker is selected from the group consisting of alginate, starch, cellulose and its derivatives (such as cellulose acetate, carboxymethyl cellulose, and methyl cellulose), xanthan gum, dextran, carrageenan, genipin, hyaluronic acid, condroitin sulfate, locust bean gum, gum tragacanth, gum arabic, curdlan, pullulan, scleroglucan, and lower methoxylpectin, glucose or ribose, native collagen, hyaluronic acid, fibrin, chitin, biotin, avidin, MATRIGEL®, HUMAN EXTRACELLULAR MATRIX®, proteoglycans, laminin, fibronectin, elastin, heparin, and chitosan, and/or combinations thereof.

The methods described herein may further comprise freezing, drying, or freeze-drying said dispersed soft tissue to produce a soft tissue support and/or implant. In another embodiment, the freezing and freeze-drying may be conducted at a controlled freezing/cooling rate. The controlled freezing/cooling rate may be between from about 1° C. to 20° C. per minute, from about 2° C. to 10° C. per minute, from about 3° C. to 10° C. per minute, from about 3° C. to 6° C. per minute. In some embodiments, the soft tissue support and/or implant may be freeze-dried to a point such that the freeze-dried fragments have an average residual moisture of less than about 10, 5, 4, 3, 2, 1, 0.5, or 0.1 wt %. In further embodiments, the soft tissue support and/or implant may be dried, and/or freeze-dried to a point such that the dried or freeze-dried fragments have residual moisture from about 0.01% to 10%, from about 0.01% to 5%, from about 0.01% to 3%, from about 0.1% to 3%, from 0.5% to 3%, or from 1% to 3%.

In some embodiments, the soft tissue support may be desiccated. For example, the freeze-dried soft tissue support may be desiccated in an oven, a desiccator, or in package(s) with desiccant (in packets or other forms), and maintained at a temperature from 10° C. to 100° C., from 15° C. to 60° C., from 20° C. to 55° C., or from 20° C. to 40° C. for a period of time of from 7 days to 5 years, from 14 days to 120 days, or from 14 days to 70 days.

In another aspect, the dispersed soft tissue described herein consists essentially of and/or consists of the one or more soft tissue(s); and solution or solvent. In some embodiments, the soft tissue support and/or implant consists essentially of and/or consists of components from the one or more soft tissue(s). The term "essentially consisting of" defines the scope of the soft tissue support and/or implant to include additional elements that do not materially affect the porosity or void fraction of the soft tissue support and/or implant consisting of initial elements. For example, the dispersed soft tissue consisting essentially of one or more soft tissue(s) may include elements in addition to the one or more soft tissue(s) that do not materially affect the porosity or void fraction of the dispersed soft tissue consisting of the one or more soft tissue(s). Materially affecting the porosity or void fraction herein means changing the porosity or void fraction at least by about 0.5, 1, 2, 3, 4, 5, 7, 9, 10, 12, 15, 20, 25, 30, or 40%.

In some embodiments, the density of the soft tissue support and/or implant is about 0.001 g/cm3, 0.01 g/cm3, 0.05 g/cm3, 0.1 g/cm3, 0.5 g/cm3, 0.7 g/cm3, 0.9 g/cm3 or more in a dry state. In additional embodiments, the density of the soft tissue support and/or implant is about 0.002 g/cm3, 0.02 g/cm3, 0.06 g/cm3, 0.3 g/cm3, 0.6 g/cm3, 0.8 g/cm3, 0.9 g/cm3, 1.0 g/cm3, 1.2 g/cm3, 1.5 g/cm3 or less in a dry state. In further embodiments, the density of the soft tissue support and/or implant is from about 0.01 g/cm3 to about 1 g/cm3, from about 0.01 g/cm3 to about 1 g/cm3, from about 0.02 g/cm3 to about 0.5 g/cm3, from about 0.02 g/cm3 to about 0.2 g/cm3, from about 0.0.3 g/cm3 to about 0.2 g/cm3 in a dry state.

In some embodiments, the soft tissue support and/or implant comprises pores having an average or mode diameter of about 1, 5, 10, 100, 200, 300, 400, 500, 700, 1000, 1500, 2000, 3000, or 4000 μm or more. In additional embodiments, the soft tissue support and/or implant comprises pores having an average or mode diameter of about 2, 6, 20, 100, 200, 300, 400, 500, 700, 900, 1000, 1300, 1500, 2000, 3000, or 4000 μm or less. In further embodiments, the soft tissue support and/or implant comprise pores having an average or mode diameter from about 1 μm to 4000 μm, from 1 μm to 1000 μm, from about 10 μm to 1000 μm, from about 20 μm to 500 μm, from about 20 μm to 200 μm, from about 50 μm to 200 μm on an average. In some embodiments, the soft tissue support and/or implant has up to 70% of pores with a diameter less than 50 μm. In some embodiments, the soft tissue support and/or implant has more than 30% pores with a diameter from about 50 μm to 200 μm. In some embodiments, the soft tissue support and/or implant comprise more than 50% pores with a diameter from about 20 μm to 200 μm.

In some embodiments, an average void volume of the soft tissue support and/or implant is about 10, 20, 30, 40, 50, 60, 70, 80, 90, 95, 96, 97, 98, 99% or more. In additional embodiments, an average void volume of the soft tissue support and/or implant is about 10, 20, 30, 40, 50, 60, 70, 80, 90, 95, 96, 97, 98, 99% or less. In further embodiments, an average void volume of the soft tissue support and/or implant is from about 10% to about 99%, from about 30% to 99%, from about 50% to about 99%, from about 70% to 99%, from about 80% to about 99%, or from about 80% to 96%. In some embodiments, the average void volume of the soft tissue support is from about 1 cc/to 30 cc/g, from about 2 cc/g to 20 cc/g, from about 3 cc/g to 20 cc/g, from about 5 cc/g to 20 cc/g. In some embodiments, the average void volume of the soft tissue support can be controlled by adjusting the volume of liquid added to the dispersed soft tissue prior to drying or freeze drying.

In some embodiments, the soft tissue support is compressible after hydration and elastically re-formable after weight removal. The shape and dimension of the soft tissue support may elastically return to original shape and dimension after substantial compression, e.g., with 50 grams to 1000 grams, with 100 grams to 1000 grams, or with 100 grams to 500 grams; or less than 2000 grams, less than 1000 grams, or less than 500 grams. The time required to return to original shape and dimension after substantial compression may be less than 30 seconds, less than 20 seconds, less than 10 seconds, or less than 5 seconds. The dimension change of the soft tissue support may be less than 80%, less than 70%, less than 60%, less than 50%, less than 40%, less than 30%, less than 20%, or less than 10% after the weight removal.

In some embodiments, the soft tissue support is compressed before hydration to obtain a thinner soft tissue support. The compressing force may be from 1 ton to 60 tons, from 5 tons to 60 tons, from 5 tons to 55 tons, from 10 tons to 50 tons, from 10 tons to 40 tons, or from 15 tons to 35 tons. The compressed thickness may be reduced relative to the uncompressed thickness by from 10% to 95%, from 10% to 85%, from 20% to 80%, from 30% to 80%, from 40% to 90%, from 50% to 90%. The soft tissue support may be configured to retain its compressed shape while in a dehydrated state. The shape and dimension of the support may be configured to elastically return to original shape and dimension after hydration.

In some embodiments, the soft tissue support and/or implant prepared by the methods described herein may have collagen fiber, collagen fiber bundle dimensions or diameters more similar to its natural state, compared to some other processing techniques in the prior art. In some embodiments, the fibers or fiber bundles in the soft tissue support are intertwined or randomly interwoven. Previous techniques have led to a tissue fiber with smaller sizes than the natural fibers and thus may degrade faster in vivo. Moreover, the soft tissue in the methods described herein is preferably dispersed without being denatured, micronized, or cryofractured, thus preferably having no change or only minimal change of the extracellular matrix macromolecule components (for example: collagen, proteoglycan, elastin, hyaluronic acid, laminin, fibronectin, among other), and having no change or only minimal change in the relative ratio of macromolecule components in the dispersed soft tissue, and/or the soft tissue support and/or implant. In the other words, the extracellular matrix macromolecules of the resulting soft tissue support are preferably not modified (or at least not substantially modified). Dispersing the soft tissue according to the disclosed methods may open the structure of the soft tissue to facilitate cell infiltration and/or tissue-in-growth after implantation, but preferably may not modify the support and/or implant interaction at the micro scale level, unlike implants prepared by other techniques. At the same time, the fiber and/or fiber bundle dimension (e.g. diameter, or width, and length) of preferred supports and/or implants may support a framework with opened pore structure and with a network of fibers and/or fiber bundles that may provide a relatively strong and stable framework without needing additional (non-natural) crosslinking or adding a carrier. In some embodiments, the fiber or fiber bundle dimension may provide a stable framework for the support and/or implant without modifying or weakening the integrity and cohesiveness of the support and/or implant. In preferred embodiments, the structure of the support and/or implant can stay intact after rehydration and agitation in liquid, and the support and/or implant can allow for biocompatible cellular and tissue response and good volume retention after implantation in an animal. The volume retention after implantation in an animal may be measured by the largest cross-section area of the implanted support at different times after implantation. For example, the soft tissue support and/or implant may have recipient's cell infiltration and angiogenesis after 1-4 weeks of implantation, and maintain support and/or implant volume (e.g. the largest cross-section area of implanted support) from about 30% to 100% between 4 week and 24 weeks of implantation, from about 40% to 100% between 4 week and 24 weeks of implantation, or from about 50% to 100% between 4 week and 24 weeks of implantation.

In some embodiments, the soft tissue support and/or implant may comprise fibers or fiber bundles having an average diameter of about 0.1, 0.5, 1, 3, 5, 10, 20, 30, 40, 50, 60, 70, 80, 90, 100, 110, 120, 130, 140, 150, 200, 250, 300, 350, 400, 450, 500 μm or more. In additional embodiments, the soft tissue support and/or implant may comprise fibers or fiber bundles having an average diameter of about 0.1, 0.5, 1, 3, 5, 10, 20, 30, 40, 50, 60, 70, 80, 90, 100, 110, 120, 130, 140, 150, 200, 250, 300, 350, 400, 450, 500 μm or less. In further embodiments, the soft tissue support and/or implant may comprise fibers or fiber bundles having an average diameter from about 0.1 μm to about 500 μm, from about 0.1 μm to about 200 μm, from about 1 μm to about 500 μm, from about 10 μm to about 500 μm, from about 100 μm to about 1000 μm, or from about 100 μm to about 500 μm.

In some embodiments, the soft tissue support and/or implant comprises fibers and/or fiber bundles having an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or more. In some embodiments, the soft tissue support and/or implant comprises fibers and/or fiber bundles having an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or less. In additional embodiments, the soft tissue support and/or implant comprises fibers and/or fiber bundles having an average length from about 5 μm to about 50 cm, from about 100 μm to about 50 cm, from about 1000 μm to about 50 cm, from about 1 cm to about 50 cm, from about 1 cm to about 30 cm, from about 1 cm to about 20 cm, or from about 1 cm to about 15 cm.

The example methods described herein may comprise sieving the dispersed soft tissue, for example, on a sieve, mesh, or grid having pore size of about 0.5, 1, 2, 3, 4, 5, 6, 7, 8, 9, 10, 13, 16, 17, or 20 mm or less. In another aspect, the method described herein may comprise sieving the dispersed soft tissue, on a sieve, mesh, or grid having pore size of about 0.5, 1, 2, 3, 4, 5, 6, 7, 8, 9, 10, 13, 16, 17, or 20 mm or more. In another aspect, the method described herein may comprise sieving the dispersed soft tissue, on a sieve, mesh, or grid having pore size diameter from about 0.5 to 20 mm, from about 1 to 10 mm, from about 2 to 10 mm, from about 2 to 8 mm, or from about 2 to 6 mm.

In another aspect, the method described herein may further comprise placing the dispersed soft tissue in a mold having a predetermined shape, wherein the dispersed soft tissue is frozen, freeze-dried, and/or plasticized in the mold. In another aspect, the method described herein may further comprise storing the soft tissue support and/or implant prior to implanting. In some embodiments, the soft tissue support and/or implant is stored in a dry state, in cryopreservation, or in a wet state. In additional embodiments, the method describe herein may further comprise treating the soft tissue support and/or implant with a water replacing agent. In further embodiments, the soft tissue support and/or implant may be stored in a wet state. In yet further embodiments, the water replacing agent comprises one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. In another aspect, the method described herein may further comprise plasticizing the soft tissue support and/or implant as described in U.S. Pat. Nos. 6,293,970, 6,569,200, 6,544,289, 7,063,726, or U.S. Patent Application Publication No. 2010/0030340, 2014/0180437, 2011/0015757, and 2013/0218294, each of which is incorporated by reference herein by its entirety.

In another aspect, the methods described herein may also comprise treating said soft tissue support and/or implant with one or more treatment solutions before or after freezing drying, and/or freeze drying (or before or after other methods for drying the support, besides freeze drying, such as air dry or drying in a drying oven at a pre-set temperature). In some embodiments, the method described herein may also comprise treating said soft tissue support and/or implant with one or more treatment solutions after freezing, drying, and/or freeze drying before implantation. In some embodiments, the treatment solution comprises an ionic, enzymatic, or chemical crosslinking agent, a photoactive agent, or a polymer. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent comprises one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, HUMAN EXTRACELLULAR MATRIX®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid. Furthermore, it should be considered that besides freeze drying, other methods for drying the soft tissue support, such as air drying or drying in a drying oven at a pre-set temperature, can be used.

In another aspect, the method described herein may also comprise adding one or more bioactive supplement(s) to the one or more soft tissue(s), the dispersed soft tissue, or the soft tissue support and/or implant. In some embodiments, the one or more bioactive supplement(s) is selected from a group consisting of a growth or differentiation factor of the FGF family, TGF-family, amelogenin family, IGF-1, PDGF, EGF, VEGF, HGF, PTHrP, Ihh, dexamethasone, insulin, transferrin, selenium, ITS, or ascorbate. The bioactive supplements may be growth factors, differentiation factors, cytokines, anti-microbial agents, enamel matrix derivative (EMD), or anti-inflammatory agents. The growth or differentiation factors may be for example, a growth factor of the FGF-family or TGF-family, IGF-1, PDGF, EGF, VEGF, HGF, PTHrP, Ihh (Indian Hedgehog Homolog), dexamethasone, insulin, transferrin, selenium, ITS supplement, ascorbate, or a combination thereof. The cytokines may include GM-CSF, G-CSF, TNF-α, IL-1β, IL-4, IL-6, IL-8, IL-10, SLP1, MCP1, MIP-1a, MIP-2, IL-18, angiopoietin, KGF, endothelin, IFN-α, or IFN-β. Examples of anti-inflammatory agents may include an IL-1βR antibody, TNF-α receptor antagonist, cyclooxygenase-2 specific inhibitors, MAP kinase inhibitors, NO synthase inhibitors, NF-κB inhibitors, or inhibitors of MMP. There are various fibroblast growth factors. As an example, the human FGF-family includes 22 members, FGF-1 through FGF-23. (There is no human FGF-15 because FGF-15 is the mouse ortholog of human FGF-19.) Examples of members of the TGF-family may include TGF-α and TGF-β superfamily. The TGF-β superfamily includes TGF-βs (such as TGF-β1, TGF-β2, TGF-β3), activins, inhibins, bone morphogenic factors (BMPs), modified BMPs, anti-mullerian hormone (AMH), myostatins, and others. There are 20 isotypes of BMPs. They may be separated into four subfamilies, for example, (1) BMP2 and BMP4; (2) BMP3 and BMP3B (also known as growth/differentiation factor 10 (GDF10)); (3) BMPs 5, 6, 7 and 8; and (4) GDFs 5, 6, and 7. In additional embodiments, the method described herein may also comprise adding one or more bioactive supplement(s) extracted from tissue comprising demineralized bone matrix, basement membrane, or submucosa matrix. In further embodiments, the method described herein may also comprise adding one or more antioxidants including, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

In another aspect, the method described herein may also comprise adding one or more agent(s) that have bioactive supplement binding site(s) to the one or more soft tissue(s), the dispersed soft tissue, or the soft tissue support and/or implant. In some embodiments, the agents having bioactive supplement binding site(s) may comprise hyaluronan, heparin, heparin sulfate, keratin sulfate, dermatan sulfate, chondroitin sulfate, betaglycan, heparan sulfate proteoglycan, syndecan, biglycan, or decorin. In additional embodiments, the agent(s) that have bioactive supplement binding site(s) increases the affinity of growth factors, differentiation factors, cytokines, anti-microbial agents, or anti-inflammatory agents to said soft tissue support and/or implant.

In another aspect, the method described herein may also comprise cutting the one or more soft tissue(s), prior to dispersing the soft tissue, to have a dimension of length and/or diameter of about 0.5, 1, 5, 10, 20, 50, 100, 200, 500 mm or more on average. In additional embodiments, the method described herein may also comprise cutting the one or more soft tissue(s) to have a dimension of about 1, 5, 10, 20, 50, 100, 200, 550 mm or less on average. In further embodiments, the method described herein may also comprise cutting the one or more soft tissue(s) to have a dimension from about 1 mm to about 60 cm, from about 1 mm to about 50 cm, from about 1 cm to about 30 cm, from about 1 cm to about 20 cm, or from about 1 cm to about 10 cm on average.

In another aspect, the method described herein may comprise cleaning and disinfecting the one or more soft tissue(s). In another aspect, the method described herein may also comprise cleaning and disinfecting the soft tissue, and removing extraneous tissues associated with the soft tissue. Soft tissues may be cut into small pieces to produce crudely fragmented soft tissue, and optionally triturated and washed with distilled/deionized endotoxin-free water and/or an aqueous solution, such as isotonic saline, among others. In processing, multiple "washes" or "cleaning" may be affected using volumes of aqueous solution that are 2, 5, 10, or 20 times the approximated volume of the tissue being processed, in some embodiments. The use of three such processing steps may affect an approximate 1:100, 1:500 or 1:1000 dilution of associated solubilizable elements rendering the tissue essentially free from such solubilizable elements. The dispersed soft tissue may include soft tissue that has been reduced to fibers, bundle, sheets, and other components that are uniformly small and evenly distributed. The dispersed soft tissue may optionally include at least one of water, aqueous solutions, for instance isotonic saline, and water miscible polar organic solvents. In some embodiments, the dispersed soft tissue and, optionally, at least one of a water miscible polar organic solvent, water and an aqueous solution, may be prepared by shear-induced shredding of soft tissue. A conventional blender may be used in preparing the dispersed soft tissue, in certain embodiments. In a preferred embodiment, the dispersion speed is set from low to medium speed for a conventional blender. In another aspect, the method described herein may also comprise devitalizing or decellularizing the one or more soft tissue(s) to remove cellular components in accordance with the methods described in U.S. Pat. Nos. 6,734,018, 7,338,757, 8,574,826, 6,743,574, and 8,563,232, and U.S. Patent Application Publication No. 2014/0065238A1 and 2014/0154663A1, each of which is incorporated by reference herein in its entirety. A devitalization process may be performed without damage to matrix and/or tissue structure of the soft tissue and may employ detergents, sarcosinates, endonuclease, and disinfecting agents. The matrix structure may include collagens, hyaluronins, elastins, fibronectins, laminins, mucopolysaccharides and proteoglycans, among other components. Soft tissue that is devitalized may have a thickness of about 30, 20, 15, 10, 8, 5, 3, 2, 1, 0.5, 0.1, 0.05 mm or less, in certain embodiments. Soft tissue that is devitalized may also have a thickness of about 30, 20, 10, 8, 5, 3, 2, 1, 0.5, 0.1, 0.05 mm or more. In another aspect, the method described herein may also comprise placing the soft tissue support and/or implant in designed packages that will fit the shapes and dimensions of the soft tissue support and/or implant, and maintain the shapes and dimension until implantation (See, e.g., WO2014130953, incorporated herein by reference). In another aspect, the method described herein may also comprise sterilizing the one or more soft tissue(s), the dispersed soft tissue, or the soft tissue support and/or implant. Sterilization may involve the use of ionizing radiation, in some embodiments. In other embodiments, the absorbed dose of ionizing radiation may be between about 8.0 KGy and about 50 KGy, between about 8.0 KGy and about 25 KGy, or between about 8.0 KGy and about 18 KGy. In some embodiments, the sterilizing step may include placing the packaged tissue repair implants having a porous structure on dry ice and irradiating the packaged composition. In certain embodiments, sterilization may be performed at a temperature of between about −20° C. and −50° C. The implants may be sterilized using gamma irradiation, disinfecting agents, supercritical carbon dioxide, ethylene oxide, or electronic-beam.

In another aspect, the method described herein may comprise adding one or more bone or cartilage fragment material(s) to the one or more soft tissue(s), the dispersed soft tissue, or the soft tissue support and/or implant. In some embodiments, bone fragments material(s) comprise one or more selected from the group consisting of bone, cortical bone, cancellous bone, cortical cancellous bone, ceramics, hydroxyapatite, calcium phosphate, calcium sulfate, and calcium carbonate. The bone may be demineralized bone or non-demineralized bone. "Demineralized bone matrix (DBM)" as used herein refers to bone having less than about 8 wt % residual calcium. Demineralization involves treating a bone tissue to remove its inorganic mineral hydroxyapatite material. The level of demineralization of a bone tissue is defined by the amount (wt %) of residual calcium found in the demineralized bone. In some embodiments, the demineralized bone may still contain physiologically active levels of growth and differentiation factors (e.g., osteogenic/osteoinductive growth factors, such as bone morphogenetic proteins (BMPs) remaining from the initial bone even after the demineralization treatment. In further embodiments, the demineralized bone may contain collagen, glycosaminoglycans, osteocalcin, osteonectin, bone sialoprotein, osteopontin, and mixtures thereof. "Non-demineralized bone" as used in the present application refers to bone that has not been treated to remove minerals present such as, for example, hydroxyapatite. Certain soft tissue supports and/or implants may include demineralized bone particles or fibers. Demineralized bone matrix may be prepared from cleaned and disinfected bone that have been freeze-dried or not freeze-dried and ground/fractured/milled into bone particles or fibers. Bone particles may be selected by, for example, using sieving devices (i.e., mesh sieves) commercially available for obtaining particles within a desired size range. Such demineralized bone particles may have an average diameter of between about 125 microns and about 4 mm; between about 710 microns and about 2 mm; between about 125 microns and about 500 microns; between about 125 microns and about 850 microns; between about 125 microns and about 710 microns; between about 250 and 1000 microns; or between about 250 microns and about 710 microns. Certain examples may include demineralized bone particle that is commercially available. For example, a suitable demineralized bone particle that is widely and reliably available is produced by LifeNet Health, Virginia Beach, Virginia. Some soft tissue supports and/or implants may include demineralized bone fibers. In certain embodiments, the demineralized bone fibers may have an average thickness of between about 0.1 mm and about 0.3 mm and an average width of between about 0.3 mm and about 1.0 mm. The length of the fibers may vary. In some embodiments, the demineralization process begins by producing bone particles having an average diameter size range of between about 1 mm and about 2 mm or bone fibers having an average dimension of 0.1 mm to 0.5 mm thickness and an average width of about 0.3 mm to about 1 mm. The fragments may be treated with cleaning solutions. If the bone to be processed into fragments has not been previously cleaned and/or disinfected, they may be cleaned and/or disinfected by the use of detergents, hydrogen peroxides, antibiotics, acids, and/or alcohols to affect a removal of associated tissues such as bone marrow and cellular elements. Following cleaning and disinfection, these fragments (i.e., particles and fibers) may be demineralized by exposure to dilute hydrochloric acid to affect a removal/reduction of the mineral component of the bone fragments (i.e., particles and fibers). Such additional processing may, in some instances, inactivate potential viral contamination (i.e., HIV and hepatitis viruses, among others).

In another aspect, the method described herein may or may not comprise processing the dispersed soft tissue under negative hydrostatic pressure before being frozen, dried, or freeze-dried to increase porosity. Three-dimensional (3-D) macro-porous structure is designed to provide support for the cells until they are organized into a functioning tissue. After implantation, the architecture of the macro-porous structure can control the extent of vascularization and tissue ingrowth. The pore size and volume can be adjusted by adding porogens, application of inert gas, or application of a negative hydrostatic pressure before or after freeze-drying the soft tissue support and/or implant.

In some aspects, the method for forming the material of the soft tissue support may include any of the steps or processes described in U.S. Patent Application Publication No. 2018/0044629 A1, the contents of which are incorporated by reference herein in their entirety.

Figure 1B:
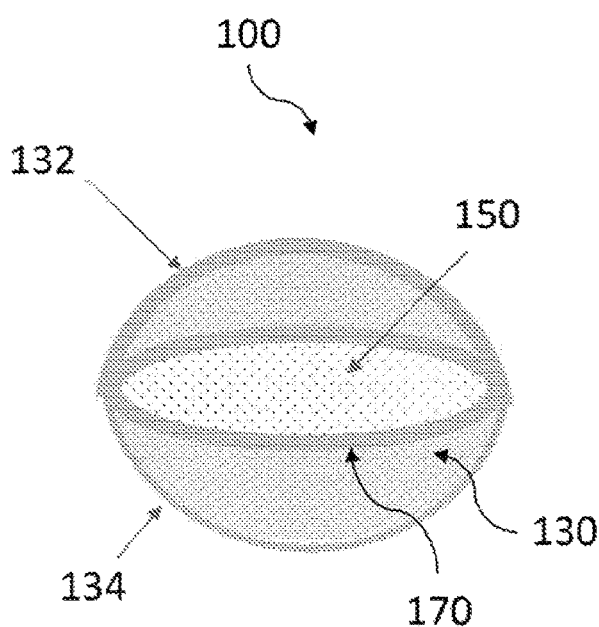
Figure 1C:
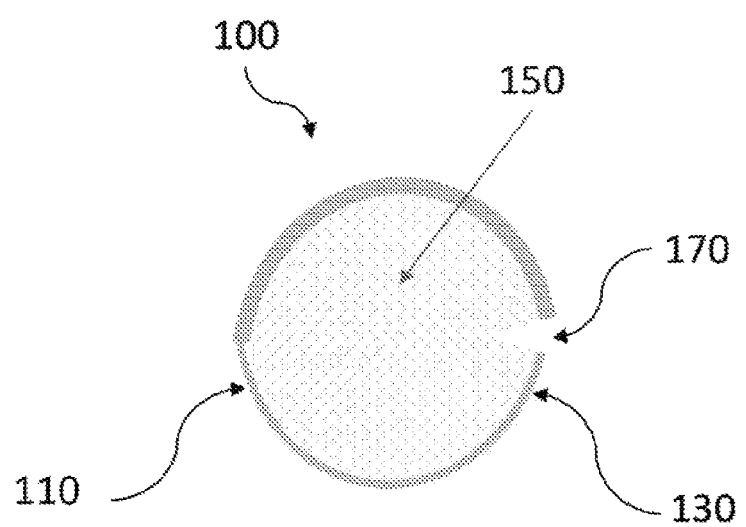

Reference now is made in detail to the examples illustrated in the accompanying drawings and discussed below. FIGS. 1A-1C illustrate an example of a soft tissue support 100. Soft tissue support 100 is a unitary piece of processed porous tissue material. Soft tissue support 100 is structured to support a corresponding implant. For example a corresponding breast implant, during and following implantation. Details regarding soft tissue support 100 are set forth below.

Soft tissue support 100 may be formed from a dispersed soft tissue material which has been manufactured according to any of the processes described herein. The dispersed soft tissue material may be frozen, freeze-dried, and/or plasticized in order to form the unitary piece of processed porous tissue material. The dispersed soft tissue material may lack one or both of a non-naturally occurring crosslinker and a non-naturally occurring carrier. The dispersed soft tissue material may be molded into any particular shape desired for soft tissue support 100.

In one embodiment, soft tissue support 100 has an anterior portion 110 and a posterior portion 130. The "anterior" and "posterior" designations may be selected and defined based on the intended orientation of soft tissue support 100 during and following implantation. Anterior portion 110 and posterior portion 130 may be connected to one another along at least a portion of their respective peripheries.

As shown in FIGS. 1A and 1B, the anterior portion 110 and posterior portion 130 have a shape which is at least partially curved. In a preferred embodiment, the shape of anterior portion 110 and posterior portion 130 is round or elliptical. Anterior portion 110 may have a thickness which is more than, less than, or equal to the thickness of posterior portion 130. Both anterior portion 110 and posterior portion 130 may have a uniform thickness or a varying thickness.

In a preferred embodiment, the anterior and posterior portions have respective upper and lower portions 112, 114, 132, 134 (based on the intended orientation of soft tissue support 100 during and following implantation) and the respective upper portions 112, 132 have a thickness which is greater than a thickness of the respective lower portions 114, 134. Such a structure may improve the stability of soft tissue support 100 during and following implantation, and the ability of soft tissue support 100 to support a corresponding implant. In an alternative embodiment, the respective upper portions 112 and 132 of anterior portion 110 and posterior portion 130 may have a thickness which is less than or equal to a thickness of the respective lower portions 114, 134.

Anterior portion 110 and posterior portion 130 define a cavity 150 therebetween. Cavity 150 is sized to receive a breast implant therein. Cavity 150 is defined by the shape and structure of the unitary piece of processed porous tissue material. Soft tissue support 100 does not use sutures, adhesives, fasteners, or other separate structures to create or define cavity 150.

The shape of cavity 150 may be determined or correspond to the shape of anterior portion 110 and posterior portion 130. Cavity 150 may have a shape which is at least partially curved. In a preferred embodiment, the shape of cavity 150 is round or elliptical. Cavity 150 may have a volume of from 40 to 1000 cubic centimeters, and more preferably, from 45 to 900 cubic centimeters, from 50 to 850 cubic centimeters, from 100 to 850 cubic centimeters, or from 200 to 850 cubic centimeters. In a particularly preferred embodiment, the shape, size, and dimensions of cavity 150 are selected to closely correspond to or match the shape, size, and dimensions of a corresponding breast implant or other implant which will be inserted into cavity 150.

Cavity 150 has at least one opening 170 extending through the unitary piece of processed porous tissue material to allow cavity 150 to communicate with the environment outside of soft tissue support 100. Opening 170 is sized to receive the breast implant therethrough. Opening 170 may have a cross-sectional area which is less than a cross-sectional area of cavity 150 when not under external stress or strain, in order to retain the implant within cavity 150 after insertion. In some examples, the opening 170 of cavity 150 is from 50% to 100% covered, e.g., by posterior portion 130 of soft tissue support 100.

In one embodiment, opening 170 is provided at a periphery of the processed porous tissue material between anterior portion 110 and posterior portion 130, or in a region of processed porous tissue material forming a connection between anterior portion 110 and posterior portion 130. In another embodiment, opening 170 is provided in posterior portion 130. Forming opening 170 in posterior portion 130 may desirably expose a portion of the implant in cavity 150 to the musculature and/or subcutaneous tissue of the subject, and thereby enhance post-implantation adhesion and support of the implant.

Opening 170 may form an open portal when not under external stress or strain, as shown in FIG. 1B. In such an embodiment, the material of soft tissue support 100 may encapsulate less than an entirety of the corresponding implant when the implant is received in cavity 150. For example, soft tissue support 100 may cover or encapsulate 50% or more, 60% or more, 70% or more, 80% or more, 90% or more, 95% or more, or 99% or more of the corresponding implant. Such coverage can be obtained by the chosen shape and size of soft tissue support 100, without the use of sutures, staples, glues, or other fasteners, adhesives, or other fixing structures.

Figure 2A:
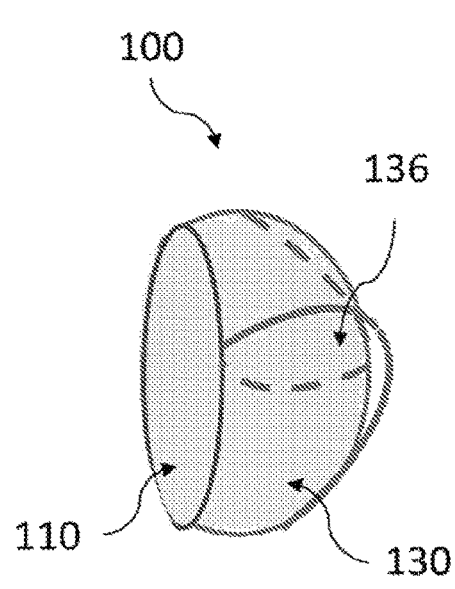
FIGS. 2A and 2B show an example of another soft tissue support.
Figure 2B:
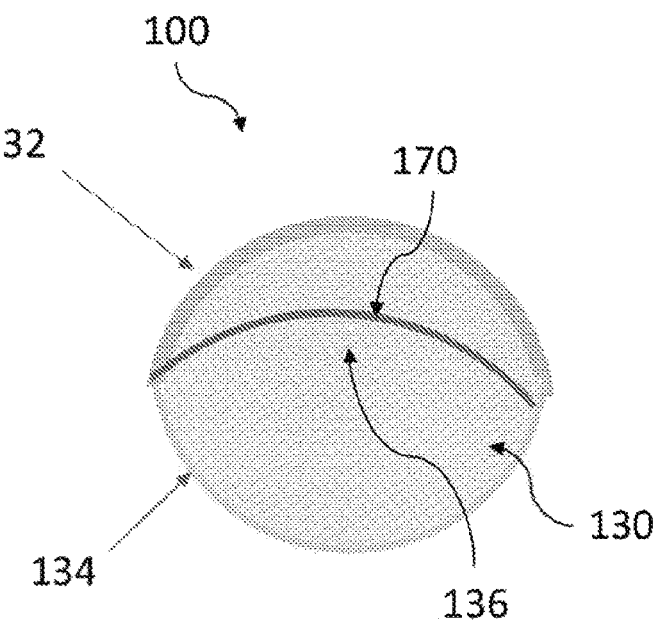

Alternatively, opening 170 may be substantially closed or sealed by a portion of the soft tissue support 100 when not under external stress or strain. In this embodiment, soft tissue support 100 can be stretched, flexed, or otherwise manipulated in order to enlarge opening 170 by an amount sufficient to permit insertion of a corresponding implant through opening 170 into cavity 150. In a preferred embodiment shown in FIGS. 2A and 2B a section 136 of posterior portion 130 substantially closes opening 170 when not under external stress or strain, such that soft tissue support 100 covers or encapsulates up to 100% of the corresponding implant.

Figure 3:
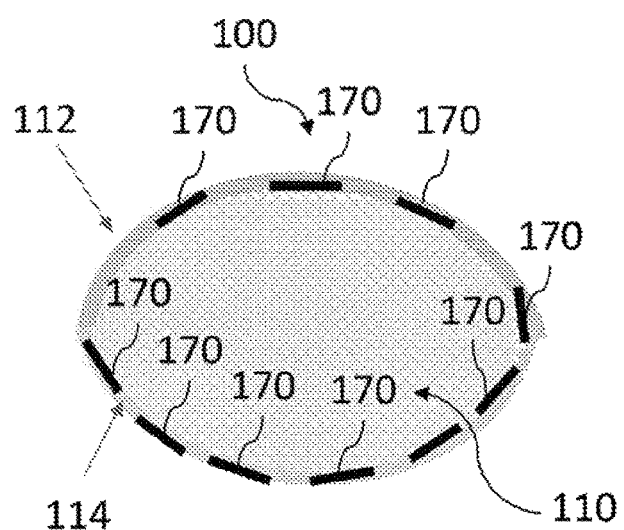
FIG. 3 shows an example of another soft tissue support.

In a further embodiment, cavity 150 includes multiple openings 170 extending through the unitary piece of processed porous tissue material, as shown in FIG. 3. In this embodiment, cavity 150 may include one opening (e.g., in posterior portion 130) which is sized to receive the breast implant therethrough, and a plurality of additional openings or slits 170 distributed around a periphery of the processed porous tissue material, e.g., between anterior portion 110 and posterior portion 130. These openings 170 may be sized and positioned for receiving suture tabs of the implant therethrough. In such an embodiment, suture tabs of the corresponding implant may extend out of cavity 150 through openings 170, to allow the implant to be sutured directly during implantation.

FIGS. 4A-4D illustrate components of an example of a soft tissue implant 300. Implant 300 includes a soft tissue support 310 and a breast implant 330. Details regarding soft tissue implant 300 are set forth below.

Soft tissue support 310 may be any soft tissue support described herein, and may include any of the features set forth above with respect to soft tissue support 100. Soft tissue support 310 may be a unitary piece of processed porous tissue material, such as dispersed soft tissue material. Soft tissue support 310 is structured to support breast implant 330 during and following implantation.

In one embodiment, soft tissue support 310 has an anterior portion 312 and a posterior portion 314 connected to one another along at least a portion of their respective peripheries, as shown in FIGS. 4A and 4B. Anterior portion 312 and posterior portion 314 define a cavity 316 therebetween. Cavity 316 is sized to receive breast implant 330 therein. The shape, size, and dimensions of cavity 316 are selected to closely correspond to or match the shape, size, and dimensions of breast implant 330. Cavity 316 has at least one opening 318 extending through the unitary piece of processed porous tissue material to allow cavity 316 to receive breast implant 330.

Breast implant 330 is positioned within cavity 316 of soft tissue support 310. Breast implant 330 may be any conventional breast implant. Breast implant 330 may be formed from medical grade, biocompatible materials. Suitable implants for use as breast implant 330 include, for example, silicone or saline-based breast implants. Other suitable implants will be understood and recognizable from the description herein.

Figure 5A:
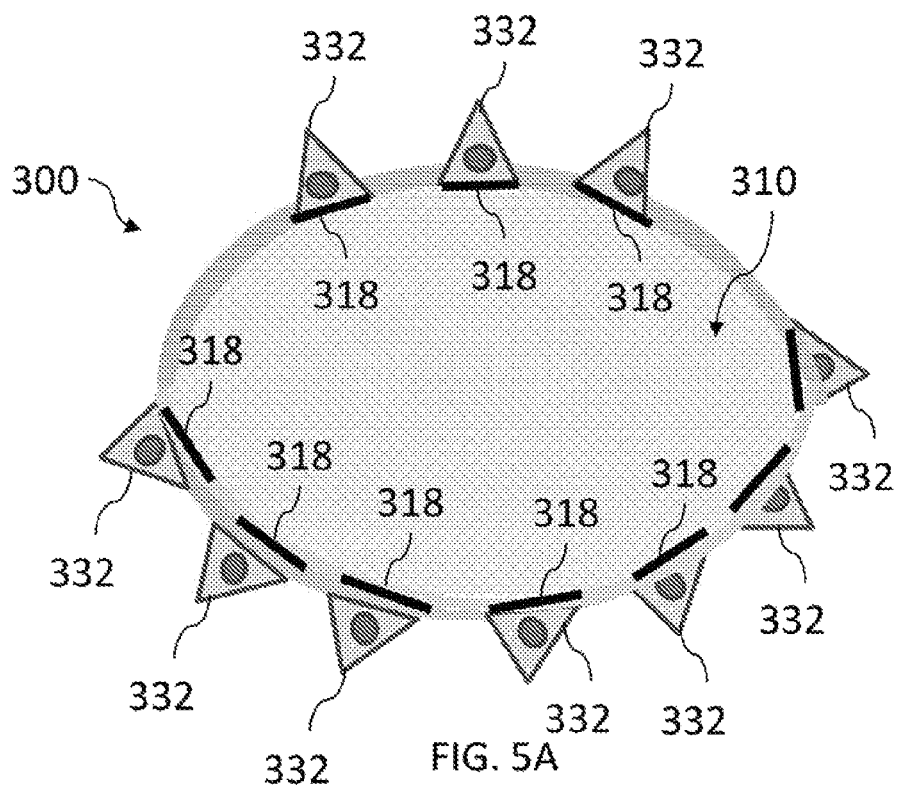
FIGS. 5A and 5B show an example of a soft tissue implant incorporating the soft tissue support of FIG. 3.
Figure 5B:
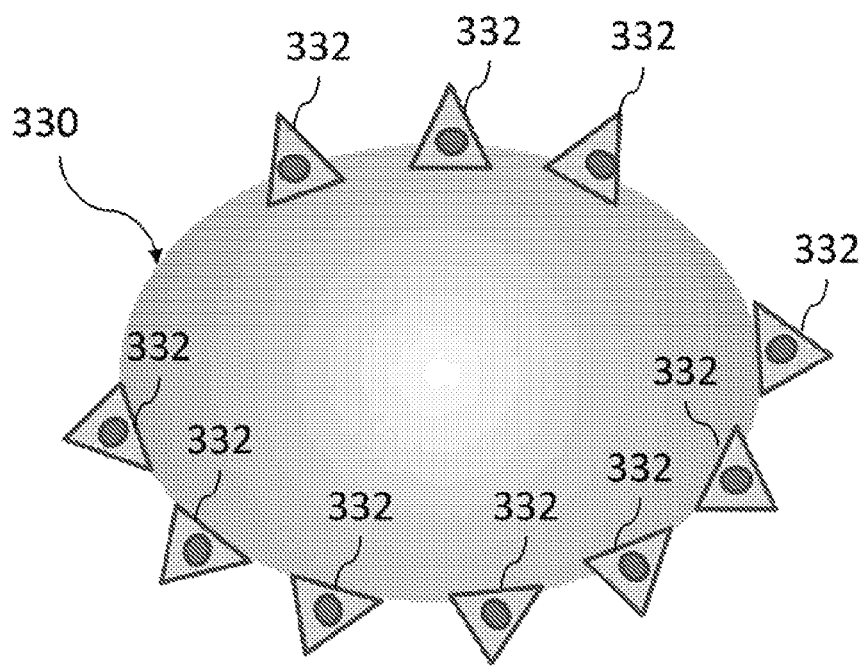

In one embodiment, breast implant 330 includes a plurality of suture tabs 332 distributed around a periphery thereof, as shown in FIGS. 5A and 5B. Suture tabs 332 are provided to enable breast implant 330 to be sutured directly to the musculature and/or subcutaneous tissue of the subject during implantation. In this embodiment, cavity 316 includes multiple openings 318 distributed around a periphery of the processed porous tissue material. These openings 318 are sized and positioned to receive respective ones of the suture tabs 332 of breast implant 330, such that suture tabs 332 extend out of cavity 316 through openings 318 when breast implant 330 is positioned within cavity 316.

Soft tissue implant 300 may further include a soft tissue graft 350. Soft tissue graft 350 comprises processed tissue material which is configured to support soft tissue support 310 and breast implant 330. Soft tissue graft 350 may advantageously provide a sling or cradle for soft tissue support 310 and breast implant 330, so that soft tissue support 310 and breast implant 330 need not be directly sutured during implantation. In this embodiment, soft tissue graft 350 may be sutured to the musculature and/or subcutaneous tissue of the subject during implantation, and then be used to hold and/or support soft tissue support 310 and breast implant 330.

Soft tissue graft 350 may have a contour which follows at least a portion of a contour of anterior portion 312 and/or posterior portion 314 of soft tissue support 310 in order to support soft tissue support. Soft tissue graft 350 may further be configured to be formed in and maintain a desired three-dimensional shape and/or contour. The shape and/or contour of soft tissue graft 350 may be selected based on the expected shape and/or contour of soft tissue graft 350 following implantation. Soft tissue graft 350 can then be stored and/or maintained in this shape/contour until ready for implantation. This contouring may be helpful in order to model the intra-operative positioning of the soft tissue graft prior to implantation, while the processed tissue material is packaged. This contouring may further be configured assist in simulating an intraoperative appearance of soft tissue graft 350, in order to promote ease of use.

In a preferred embodiment, soft tissue graft 350 has a contour corresponding to a lower portion of soft tissue support 310. In a particular embodiment, opening 318 of soft tissue support 310 may be provided in a lower portion of anterior portion 312 or posterior portion 314, or in a lower periphery of soft tissue support 310 between anterior portion 312 and posterior portion 314. In this embodiment, soft tissue graft 350 supports the lower portion of soft tissue support 310 and also covers opening 318 of soft tissue support 310, in order to better retain breast implant 330 in cavity 316 of soft tissue support 310.

In some examples, soft tissue graft 350 can be cut in such a way that allows for suturing zones on the graft without adversely impacting the biomechanical strength of the graft, and without impacting the placement of apertures in the soft tissue. The final soft tissue grafts allow for intra-operative suturing at an edge of the graft, while eliminating risk of pull-out of sutures through apertures in the graft.

In some examples, soft tissue graft 350 may have a concave shape. The concave design of certain examples allows for maximum utilization of tissue, minimizing wastage of donated tissue. The concave shape allows for intraoperative shape adjustment based on patient requirements/physiology.

In some examples, soft tissue support 310 and/or soft tissue graft 350 may include apertures. The apertures are designed to minimize stress concentrations in the soft tissue. The apertures may minimize the number of drains used post-operatively. The apertures may further maximize post-operative incorporation and revascularization of the graft. In some examples, linear apertures are used. In other embodiments, apertures may be patterned to create 2D openings in the 3D anatomical space where utilized. Apertures may be sized to maximize opening when placed over breast implant 330 and/or soft tissue support 310 (in the case of soft tissue graft 350), and may be shaped for optimal opening when tensioned in three dimensions.

In some examples, soft tissue support 310 and/or soft tissue graft 350 can be meshed. The meshing pattern maximizes the opening area of the soft tissue graft while maintaining biomechanical integrity through suture borders and internal graft bands. The meshing pattern may be designed to enhance current and contemplated techniques in breast reconstruction. The meshing pattern may also be designed to provide controlled/defined expansion in any surgical plane.

As an example, soft tissue graft 350 may be meshed to include apertures of sufficient size and number to enable a predetermined amount of expansion in surface area of the tissue material (called a mesh expansion ratio) between an unstressed state (e.g., the surface area of the unmeshed soft tissue when no stress is applied to the soft tissue graft) and a stressed state (e.g., the surface area of the meshed soft tissue when a predetermined stress or force is applied in an in-plane direction of the soft tissue graft). As an example, unmeshed soft tissue having a surface area of 3 cm$^2$, which when meshed can stretch under a predetermined force or stress to a surface area of 6 cm$^2$, would have a mesh expansion ratio of 1:2. Soft tissue graft 350 may be meshed to enable a mesh expansion ratio of 1:1.05, 1:1.1, 1:1.2, 1:1.3, 1:1.4, 1:1.5, 1:2, 1:3, 1:4, 1:5, 1:6, 1:7, 1:8, 1:9, 1:10, 1:15, or 1:20. Soft tissue graft 350 may have a preferred mesh expansion ratio in a range of from 1:2 to 1:5. Soft tissue graft 350 may be meshed to enable a mesh expansion ratio along a major (or longer) direction of the soft tissue graft to be greater than a mesh expansion ratio along a minor (or shorter) direction of the soft tissue graft. For example, soft tissue graft may have a preferred mesh expansion ratio in a range of from 1:3 to 1:10 along a major direction of the soft tissue graft, and a preferred mesh expansion ratio in a range of from 1:1 to 1:3 along a minor direction of the soft tissue graft. Soft tissue graft 350 may be configured to retain this expansion in surface area, e.g., through processing such as dehydration prior to implantation, or through suturing during implantation.

The degree of expansion of soft tissue graft 350 may be limited by the requirement of maintaining sufficient biomechanical strength. For example, in order to maintain sufficient suture retention strength for suturing during implantation, soft tissue graft 350 should resist tearing under application of a force of between 1 N and 1000 N, and more preferably, under application of a force of between 5 N and 500 N.

In some examples, soft tissue support 310 and/or soft tissue graft 350 may include any of the features or, or may be manufactured according to any of the steps or processes described, in U.S. Patent Application Publication No. 2017/0367807 A1, the contents of which are incorporated by reference herein in their entirety.

An example shape for soft tissue graft 350 is shown in FIG. 4D. In this embodiment, soft tissue graft 350 has a surface 352 bounded by an upper concave edge 354 and a lower convex edge 356. Edges 354 and 356 share both ends; in other words, edges 354 and 356 start and end at the same points. As shown in FIG. 4D, soft tissue graft 350 is symmetrical about a line bisecting edges 354 and 356.

Edges 354 and 356 may have different radii of curvature depending on the size and shape of soft tissue support 310. In some examples, concave edge 354 may have a radius of curvature of from 25 cm to 50 cm, and more preferably, from 30 cm to 46 cm, and convex edge 356 may have a radius of curvature of from 5 cm to 15 cm, and more preferably, from 6.5 cm to 10.6 cm.

In the example shown in FIG. 4D, the surface 352 of soft tissue graft 350 includes a number of apertures 358. Apertures 358 may extend all of the way through soft tissue graft 350, or may extend only part of the way through soft tissue graft 350. Apertures 358 may each have the same shape and size, or may have different shapes and sizes. Apertures 358 may be linear, or may include a multi-directional separation or cut in surface 352. Possible shapes for the multi-directional separation include S-shapes, Z-shapes, J-shapes, L-shapes, X-shapes, omega shapes, or mirror images thereof. The positioning and density of apertures 358 on soft tissue graft 350 may be uniform across surface 352, or may vary. In some examples, no apertures are positioned within a predetermined distance from edges 354 and 356, in order to create a zone for steady and secure suturing of soft tissue graft 350 during implantation. While apertures 358 are described and illustrated with respect to soft tissue graft 350, it will be understood that soft tissue support 310 may also include apertures having any of the features and placement described with respect to apertures 358.

Soft tissue graft 350 comprises tissue material which has been processed to be suitable for implantation. Such processing may include cleaning the tissue material, disinfecting the tissue material, skiving the tissue material to a predetermined thickness, removing cellular elements and small molecular weight solutes from the tissue material (i.e. "decellularizing" the tissue material), plasticizing the tissue material, packaging the tissue material, and/or sterilizing the tissue material. During plasticization, the internal matrix of the tissue material may be impregnated with one or more plasticizers.

Figure 6:
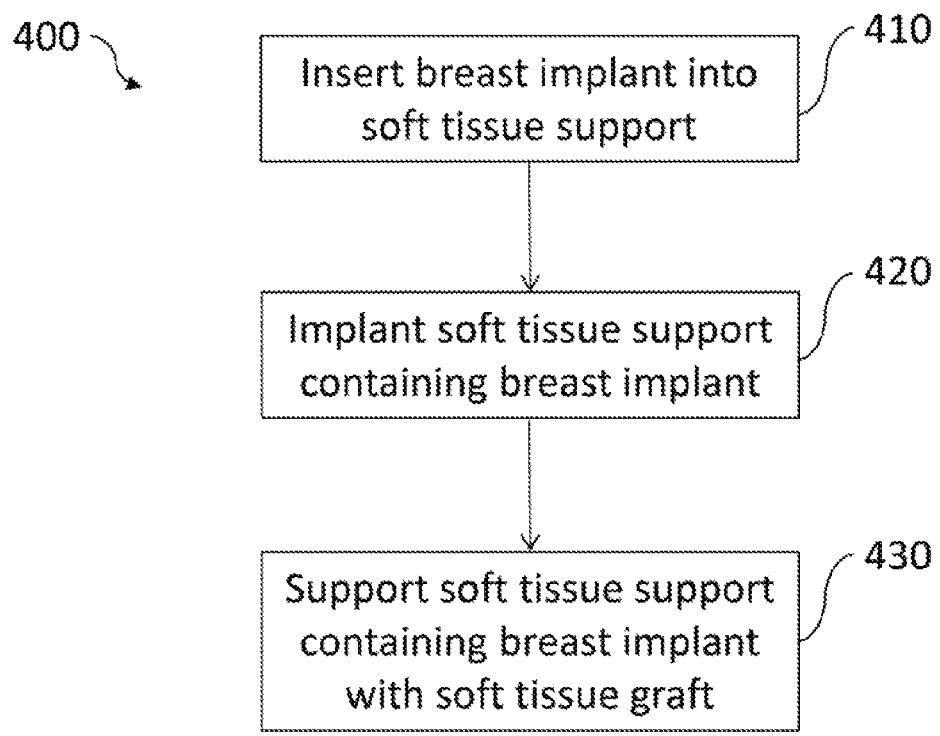
FIG. 6 is a flowchart illustrating an example of a method of use of a soft tissue support.

FIG. 6 illustrates a method 400 of use of a soft tissue support. The method includes inserting a breast implant into a soft tissue support (in step 410), and implanting the soft tissue support (in step 420). Additional details are described below with respect to the elements of soft tissue implant 300.

In step 410, a breast implant is inserted into a soft tissue support. In an example, breast implant 330 is inserted into soft tissue support 310, a unitary piece of processed porous tissue material. In particular, breast implant 330 is inserted through opening 318 into cavity 316 defined between anterior portion 312 and posterior portion 314 of soft tissue support 310. Where breast implant 330 includes suture tabs 332, this step may further include positioning breast implant 330 such that suture tabs 332 protrude through respective openings 318 distributed around a periphery of soft tissue support 310.

In step 420, the soft tissue support is implanted. In an example, soft tissue support 310 containing breast implant 330 is implanted into the subject. In a preferred embodiment, soft tissue support 310 and breast implant 330 are implanted in a subglandular insertion, in which soft tissue support 310 and breast implant 330 are positioned in front of (anterior to) a musculature of the subject. In examples where breast implant 330 includes suture tabs 332, this step may include suturing suture tabs 332 to a musculature and/or subcutaneous tissue of a subject. In other embodiments, soft tissue support 310 and breast implant 330 can be implanted by other processes, including post-pectoral muscle implant, prepectoral muscle implant, two-stage complete submuscular placement (with the use of a tissue expander), single-stage implant breast reconstruction, and/or single-stage direct to implant.

In examples in which an opening 318 is provided in the posterior portion 314 of soft tissue support 310, step 420 may include implanting soft tissue support 310 so that opening 318 faces the musculature and/or subcutaneous tissue of the subject. Such a position may expose breast implant 330 to the musculature and/or subcutaneous tissue, such that at least a portion of breast implant 330 contacts the musculature and/or subcutaneous tissue of the subject through opening 318, promoting post-implantation adhesion and support of soft tissue implant 300. Alternatively or additionally, soft tissue support 310 may be implanted including an inferior dermal flap, or with a dermal graft, in order to improve stability and adherence during or after implantation.

Method 400 may also include a step 430, in which the soft tissue support and breast impact are supported with a soft tissue graft. In an example, soft tissue support 310 and breast implant 330 are supported with soft tissue graft 350. As part of this step, soft tissue graft 350 may be positioned covering a lower portion of soft tissue support 310. When opening 318 is provided in the lower portion of soft tissue support 310, soft tissue graft 350 may be positioned to cover opening 318. In some examples, this step may include stretching or reconfiguring soft tissue graft 350 to match the contour of soft tissue support 310 including breast implant 330. Step 430 may further include suturing soft tissue graft 350 to the musculature and/or subcutaneous tissue of the subject, in order to secure soft tissue implant 300 in place.

The disclosed subject matter is not limited for use in mastopexy or reconstruction procedures. Other potential applications of the disclosed soft tissue supports, grafts, and implants will be apparent from the disclosure. Certain further examples are outlined below.

As one example, the disclosed soft tissue supports may be used in a lumpectomy procedure. The soft tissue support can be molded to contour to the surgical site to fill the defect and can be combine with synthetics to aid in imaging. After lumpectomy, the soft tissue support can placed in the area where the tumor was removed and the can include surgical marker clips imbedded in the soft tissue support so that the surgical area of tumor removal can be easily identified after surgery. The size of the soft tissue support can be easily selected and modified to match the surgical cavity. The soft tissue support can help maintain the natural shape and contour of the breast and the surgical marker clips help identify the site of interest for future imaging after lumpectomy. If radiation treatment is needed, the soft tissue support and surgical clips can help imaging to deliver more precision in the treatment planning.

As another example, the disclosed soft tissue supports may be used in a wound treatment procedure. The pore size and thickness of the soft tissue support combine to support faster cell infiltration with a thicker product that can fill deep wounds compared to current acellular dermal products that may be kept thinner to support faster incorporation. The disclosed soft tissue supports can be used when addressing a wound or surgical site over a bone or when metal or hardware are used to close the skin surface. The soft tissue support increases distance between the skin and any hardware and creates cushioning to relieve discomfort when pressure is applied to the surgical area.

As another example, the disclosed soft tissue supports may be used in a dental procedure. The soft tissue support can be used for guided bone regeneration or guided tissue regeneration which is required during certain dental procedures. Additionally, the disclosed soft tissue support can made into a collagen plug or three-dimensional structure to help prevent migration during healing.

As another example, the disclosed soft tissue supports may be used in a sports medicine or joint repair procedure. When used in combination with a scaffold such as a soft tissue graft, the soft tissue support allows incorporation of thicker tissue and the scaffold provides suture retention and tensile strength. The stiffness of the soft tissue implant supports easy alignment in the surgical site compared to a comparatively flimsy dermal sheet. The compressibility of the soft tissue implant may allow for the implant to be passed through a cannula and/or passport with minimally invasive surgery and then expanded in the surgical site. In combination with suture or tacks, the soft tissue implant can be deployed and implanted more simply, with less challenges to suture management and mixing up sutures compared to a conventional acellular dermal matrix. In combination with a deployment device, the product could be loaded in a device before surgery, then passed through the cannula and deployed into the surgical site, where it would regain a desired shape through elasticity and/or rehydration. The thickness and cushioning of the soft tissue implant may provide spacing and cushioning to align rotating joints in the appropriate plane and to reduce pain of two bones contacting one another (such as the humeral head and the acromion).

As another example, the disclosed soft tissue supports may be used in a hernia repair procedure. When used in combination with a scaffold such as a soft tissue graft or synthetic mesh, the soft tissue support allows incorporation of thicker tissue and the scaffold provides suture retention and tensile strength. The soft tissue implant can be supplied in larger sizes, and the collagen matrix of the disclosed implants may be a preferred solution when working with an infected site.

As another example, the disclosed soft tissue supports may be used in plastic surgery and/or cosmetic procedures. The compressibility of the soft tissue support allows for minimal incisions and scars. Additionally, the elasticity and cushioning of the soft tissue supports can be used for plastic and cosmetic filling and lifting. The disclosed soft tissue supports can be molded to meet need of surgical sites. The disclosed soft tissue supports can be deployed in manners similar to those used for sports medicine and joint repair procedures.

In another example, the disclosed soft tissue support may be formed in a tubular structure for tubular tissue repair and replacement such as blood vessel repair and tracheal repair or replacement. The tubular soft tissue support may be used in combination with a scaffold such as a soft tissue graft or a synthetic material in matching tubular shape. The soft tissue support can provide fast integration to the surrounding host tissue.

Figure 7:
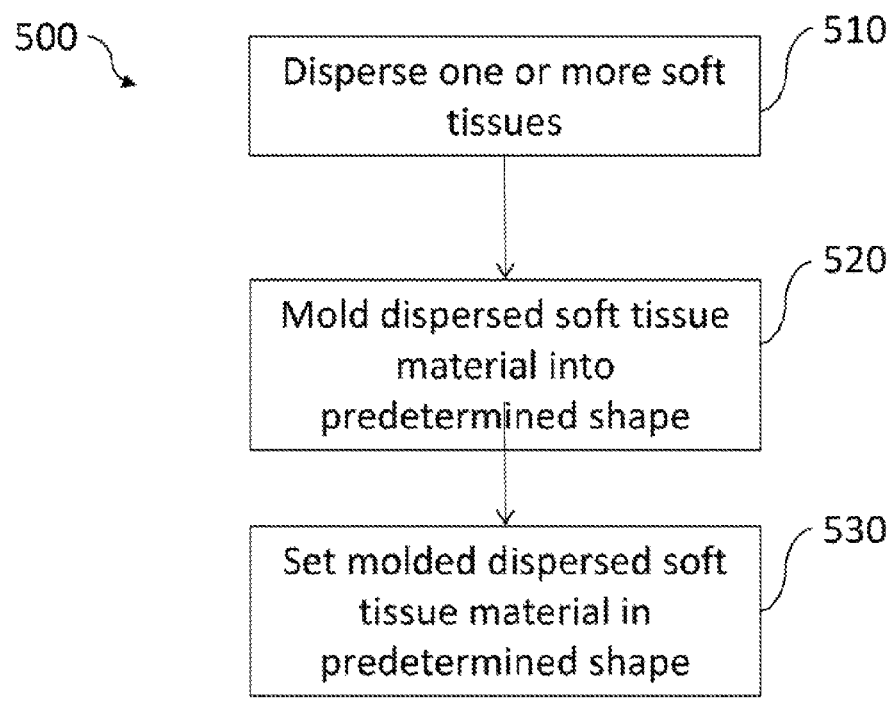
FIG. 7 is a flowchart illustrating an example of a method of making a soft tissue support.

FIG. 7 illustrates a method 500 of making a soft tissue support. The method includes dispersing one or more soft tissues, molding the dispersed soft tissue material, and setting the shape of the molded dispersed soft tissue material. Additional details are described below with respect to the elements of soft tissue implant 300.

In step 510, one or more soft tissues are dispersed. In an example, soft tissue material is dispersed to create dispersed soft tissue material. The soft tissue material may be dispersed by any of the processes disclosed herein, or by any other known process. In some examples, a non-naturally occurring crosslinker and a non-naturally occurring carrier are not added to the dispersed soft tissue material. The dispersed soft tissue material may be dispersing in a solution or solvent, so that the dispersed soft tissue material is suitable for pouring, injecting, spreading, molding, or other manipulation.

In step 520, the dispersed soft tissue material is molded into a predetermined shape for the soft tissue support. In an example, the dispersed soft tissue material is molded into the shape of soft tissue support 310, namely, a unitary piece of material having an anterior portion 312 and a posterior portion 314, the anterior and posterior portions defining a cavity 316 therebetween, the cavity 316 sized to receive a breast implant therein, the cavity 316 having at least one opening 318 sized to receive the breast implant therethrough.

Figure 8:
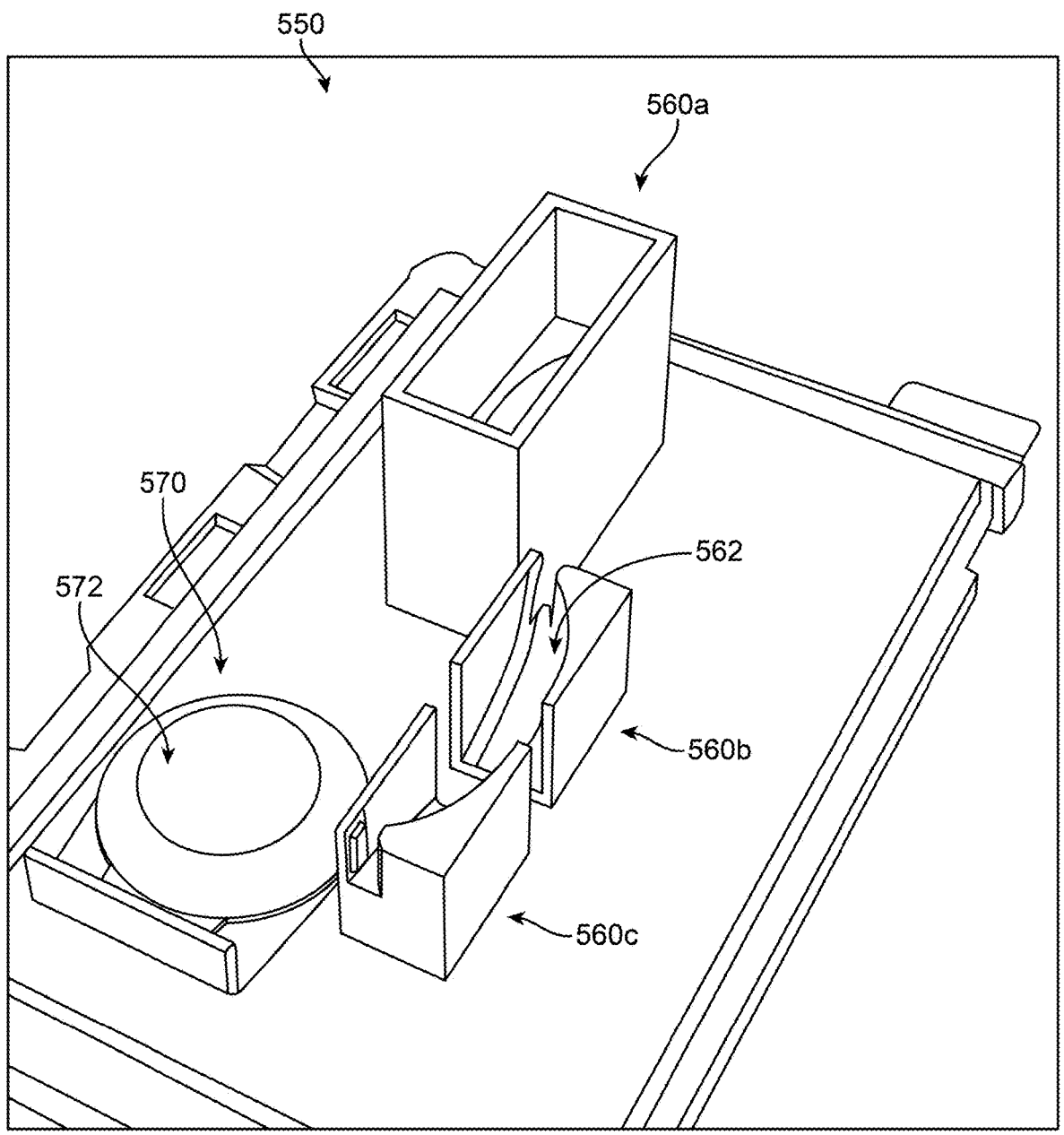
FIG. 8 shows an example of a mold for manufacturing a soft tissue support.

An example of a mold 550 for molding the shape of soft tissue support 310 is shown in FIG. 8. As shown in FIG. 8, mold 550 includes an outer mold section 560 and an inner mold section 570. Outer mold section 560 defines an outer surface 562 for molding an outer surface of anterior portion 312 and posterior portion 314 of soft tissue support 310. As shown in FIG. 8, outer mold section 560 may be formed from multiple separable components, including a body component 560a and separable end components 560b and 560c, in order to facilitate easier molding and removal of soft tissue support 310 from mold 550. Inner mold section 570 defines an inner surface 572 for molding the cavity 316 between anterior portion 312 and posterior portion 314.

In one example, dispersed soft tissue material is inserted (e.g., poured or injected) into outer mold section 560. Then, inner mold section 570 is inserted into the dispersed soft tissue material in outer mold section 560 in order to define the inner surface 572 of mold 550.

In step 530, the shape of the molded dispersed soft tissue material is set. In an example, the molded dispersed soft tissue material is frozen and/or freeze-dried and/or plasticized by any of the processes disclosed herein, or by any other known process. This step sets the shape of the molded dispersed soft tissue material, resulting in a processed porous tissue material having a shape and structure suitable for use as soft tissue support 310.

After the shape of the soft tissue material is set to form soft tissue support 310, the inner mold section 570 is removed from cavity 316. In some examples, inner mold section 570 may be formed from a flexible material which can be deflated or deformed. In these examples, inner mold section 570 is deflated or deformed in order to be removed from cavity 316 after the shape of the dispersed soft tissue material is set.

Figure 9A:
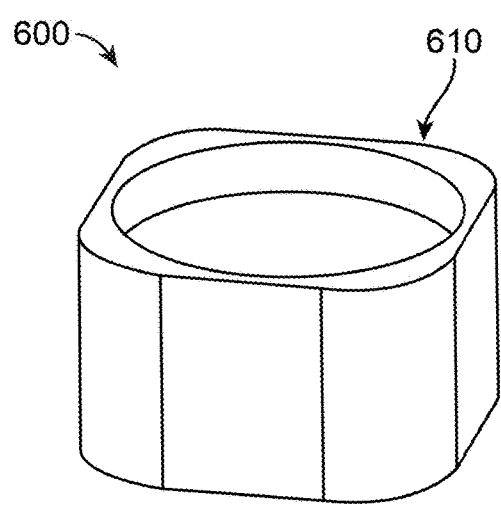
FIGS. 9A-9D show another example of a mold for manufacturing a soft tissue support.
Figure 9C:
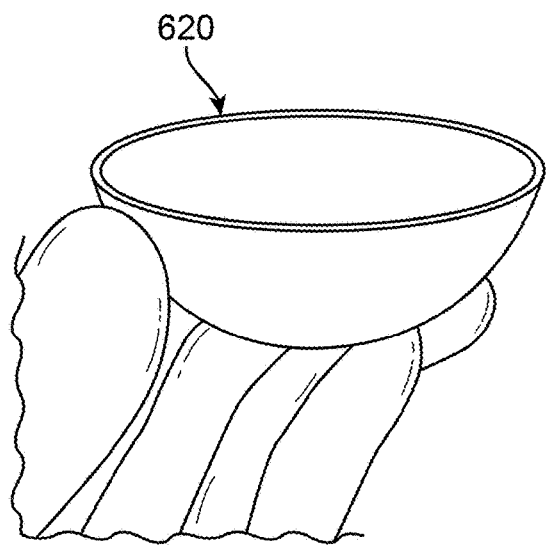
Figure 9B:
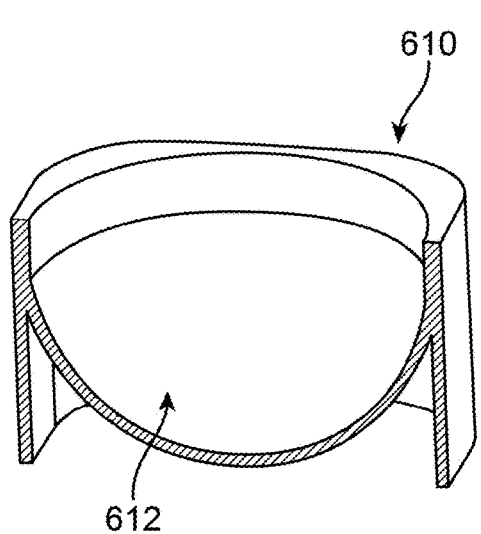

Another example of a mold 600 for molding the shape of a soft tissue support is shown in FIGS. 9A-9D. Mold 600 includes an anterior mold section 610, an inner mold section 620, and a posterior mold section 630. As shown in FIGS. 9A and 9B, anterior mold section 610 defines a surface 612 for molding an outer surface of an anterior portion of the soft tissue support. As shown in FIGS. 9A and 9B, the surface 612 may be semispherical or hemispherical in contour.

As shown in FIG. 9C, inner mold section 620 fits within anterior mold section 610, and defines an inner surface for molding the cavity between the anterior and posterior portions of the soft tissue support. As shown in FIG. 9C, inner mold section 620 may have a semispherical or hemispherical shape. The shape of inner mold section 620 may be selected to correspond to the shape of anterior mold section 610, in order to form a soft tissue portion having an anterior portion with a uniform thickness. Alternatively, the shape of inner mold section 620 may be selected to create a varying thickness for the anterior portion of the soft tissue support, as described herein.

Figure 9D:
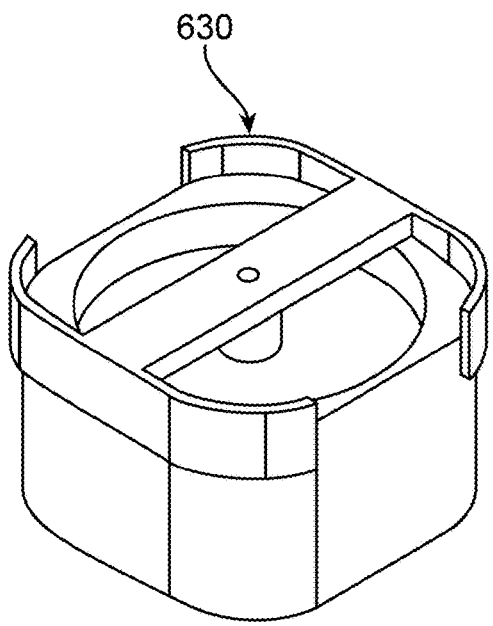

As shown in FIG. 9C, posterior mold section 630 covers the opening of anterior mold section 610. Posterior mold section 630 defines a surface for molding the posterior portion of the soft tissue support. As shown in FIGS. 9C and 9D, posterior mold section 630 may have a flat shape corresponding to a rearward shape of inner mold section 620, in order to form a soft tissue portion having a posterior portion with a uniform thickness. Alternatively, the shape of posterior mold section 630 and/or inner mold section 620 may be selected to create a varying thickness for the posterior portion of the soft tissue support, as described herein.

During molding, posterior mold section 630 may be affixed to anterior mold section 610, e.g., by screws or other fasteners. Inner mold section 620 may be suspended in place within mold 600 by affixing to one or both of anterior mold section 610 and posterior mold section 630. In a preferred embodiment, inner mold section 620 is held in a predetermined position by a screw connection with posterior mold section 630.

Molding of a soft tissue support using mold 600 may proceed in substantially the same manner as described herein with respect to the use of mold 550. After the shape of the soft tissue material is set to form the soft tissue support, inner mold section 620 is removed from the cavity, e.g., by cutting an opening in the posterior portion of the soft tissue support and removing the inner mold section 620 from through the opening.

Figure 10A:
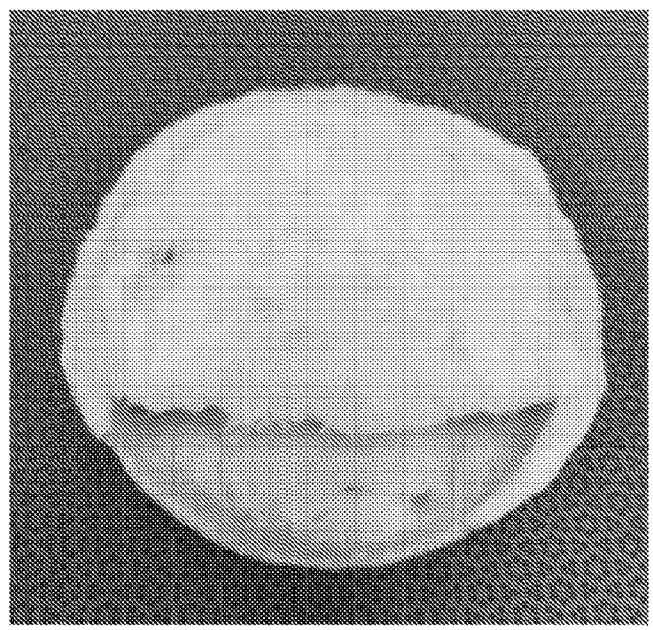
FIGS. 10A and 10B show a prototype example of a soft tissue support.
Figure 10B:
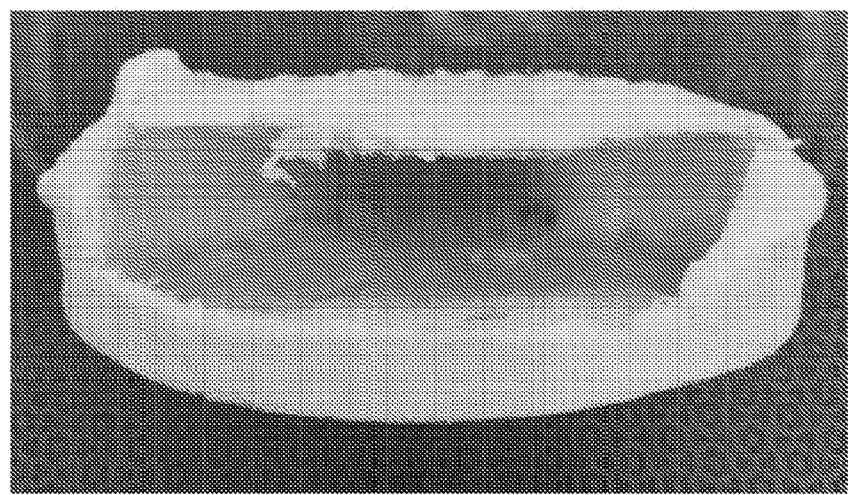
Figure 11A:
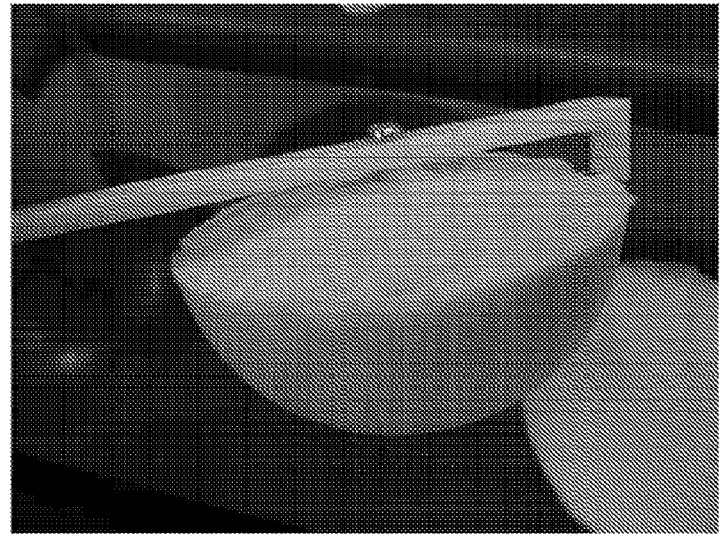
FIGS. 11A and 11B show another prototype example of a soft tissue support.
Figure 11B:
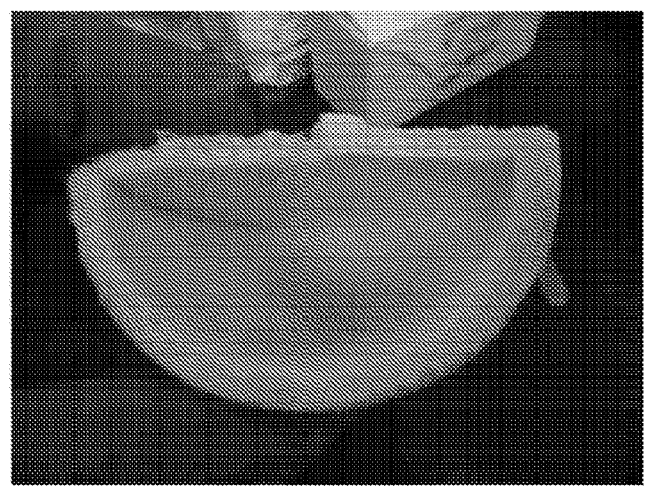

Example images of a prototype soft tissue support molded using an example mold according to the embodiment of mold 550 is illustrated in FIGS. 10A and 10B. Example images of a prototype soft tissue support molded using an example mold according to the embodiment of mold 600 is illustrated in FIGS. 11A and 11B.

FIGS. 12A-17D illustrate components of another example soft tissue implant 700. Generally, soft tissue implant 700 includes a soft tissue support 710 and a soft tissue graft 750. Soft tissue implant 700, including soft tissue support 710 and soft tissue graft 750, may include any of the features, structures, configurations, and/or characteristics described above with respect to soft tissue support 100 and/or soft tissue implant 300, including soft tissue support 310 and soft tissue graft 350. Additional details regarding soft tissue implant 700 are set forth below.

Soft tissue support 710 may be any soft tissue support described herein, and may include any of the features set forth above with respect to soft tissue support 100. Soft tissue support 710 may be a unitary piece of processed porous tissue material, such as dispersed soft tissue material. Soft tissue support 710 is structured to support a breast implant 730 during and following implantation.

In one embodiment, soft tissue support 710 has an anterior surface 712 and a posterior surface 714 connected to one another along at least a portion of their respective peripheries. Posterior surface 714 defines a cavity 716 in the posterior portion of soft tissue support 710. Cavity 716 is sized to receive breast implant 730 therein.

Soft tissue support 710 has a shape that is at least partially curved. Likewise, cavity 716 has a shape which is at least partially curved so as to correspond to a contour of soft tissue support 710. The shape, size, and dimensions of cavity 716 are selected to closely correspond to or match the shape, size, and dimensions of breast implant 730.

Cavity 716 may have at least one opening 718 defined by posterior surface 714 to allow cavity 716 to receive breast implant 730. In some examples, opening 718 may be at least partially (e.g., at least 10%, at least 20%, at least 30%, at least 40%, at least 50%, at least 60%, at least 70%, at least 80%, at least 90%, or 100%) covered by a posterior portion of soft tissue support 710, in order to shield breast implant 730 or retain breast implant 730 within cavity 716. In other examples, opening 718 may be omitted entirely, such that cavity 716 is defined entirely within soft tissue support 710. In such examples, soft tissue support 710 may be formed surrounding or encapsulating breast implant 730.

Breast implant 730 can be positioned within cavity 716 of soft tissue support 710 prior to implantation. Breast implant 730 may be any conventional breast implant. Breast implant 730 may be formed from medical grade, biocompatible materials. Suitable implants for use as breast implant 730 include, for example, silicone or saline-based breast implants. Other suitable implants will be understood and recognizable from the description herein.

Soft tissue graft 750 comprises processed tissue material which is configured to support soft tissue support 710 and breast implant 730. Soft tissue graft 750 may advantageously provide a sling, cradle, or scaffold for soft tissue support 710 and breast implant 730, so that soft tissue support 710 and breast implant 730 need not be directly sutured during implantation. In this embodiment, soft tissue graft 750 may be sutured to the musculature and/or subcutaneous tissue of the subject during implantation, and then be used to hold and/or support soft tissue support 710 and breast implant 730.

Soft tissue graft 750 may have a contour which follows at least a portion of a contour of anterior surface 712 and/or posterior surface 714 of soft tissue support 710 in order to support soft tissue support. In a preferred embodiment, soft tissue graft 750 is has a contour corresponding to the contour of the anterior surface 712 of soft tissue support 710. In this embodiment, soft tissue graft 750 does not cover or otherwise interfere with the opening 718 defined in the posterior surface 714 of soft tissue support 710, in order to allow easy insertion of breast implant 730 into cavity 716 prior to implantation.

In some examples, soft tissue graft 750 may have a concave shape. The concave design of certain examples allows for maximum utilization of tissue, minimizing wastage of donated tissue. The concave shape allows for intraoperative shape adjustment based on patient requirements/physiology.

In some examples, soft tissue graft 750 is positioned along and/or adhered to anterior surface 712 of soft tissue support 710. In other examples, soft tissue graft 750 is positioned along and/or adhered to posterior surface 714 of soft tissue support. In still other examples, soft tissue graft 750 is embedded within soft tissue support 710 between anterior surface 712 and posterior surface 714. When needed for support or otherwise desired, multiple meshed soft tissue grafts 750 may be used and provided in multiple different ones of the above positions relative to soft tissue support 710.

Soft tissue graft 750 may be meshed in order to form apertures in soft tissue graft 750. The meshing pattern maximizes the opening area of soft tissue graft 750 while maintaining biomechanical integrity through suture borders and internal graft bands. The meshing pattern may be designed to enhance current and contemplated techniques in breast reconstruction. The meshing pattern may also be designed to provide controlled/defined expansion in any surgical plane. In some examples, the meshing may form linear apertures. In other examples, the meshing may use apertures patterned to create 2D openings.

In some examples, soft tissue support 710 and/or soft tissue graft 750 may include any of the features or, or may be manufactured according to any of the steps or processes described, in U.S. Patent Application Publication No. 2017/0367807 A1, the contents of which are incorporated by reference herein in their entirety.

Examples of soft tissue graft 750 are shown in FIGS. 12A-12D. In this embodiment, soft tissue graft 750 has a surface 752 bounded by a peripheral edge 754.

Figure 12A:
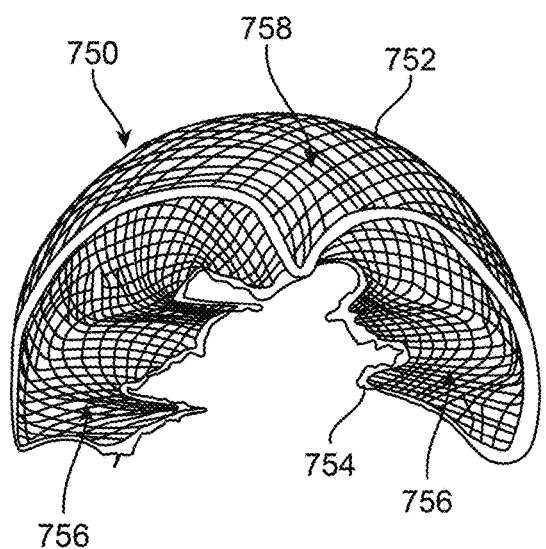
FIGS. 12A-12D show examples of a soft tissue graft.

In the example shown in FIG. 12A, surface 752 has at least a partially spherical or ellipsoidal contour which is designed to follow at least a portion of a contour of soft tissue support 710. Soft tissue graft 750 is configured to maintain this three-dimensional shape and contour, e.g., through dehydration. Soft tissue graft 750 has a suture zone 756 formed adjacent peripheral edge 754 to facilitate suturing soft tissue graft 750 during implantation.

Figure 12B:
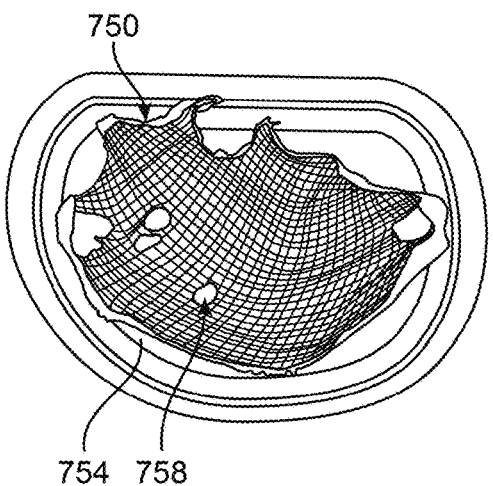

In the example shown in FIG. 12B, soft tissue graft 750 has a contour as described above with respect to the soft tissue graft of FIG. 12A. Soft tissue graft 750 of FIG. 12B is meshed in an asymmetrical pattern, to promote additional stretching and/or coverage in predetermined locations.

Figure 12C:
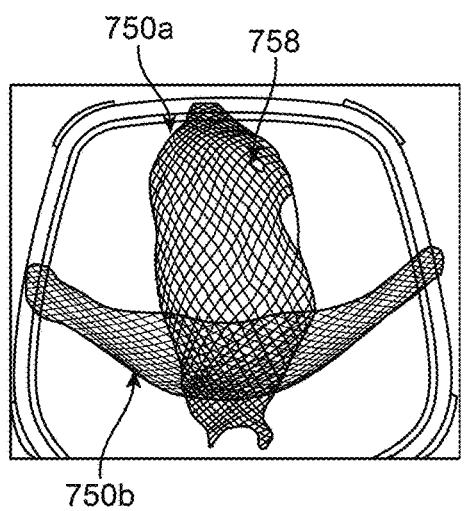

In the example shown in FIG. 12C, soft tissue graft 750 is formed from a pair of elongate portions 750a and 750b. Elongate portions 750a and 750b may be integrally formed, may be coupled to one another, or may be separate from one another. As shown in FIG. 12C, a first elongate portion 750a has a major axis (i.e., an axis which extends along the direction of elongation of portion 750a) which is configured to extend along soft tissue support 710 in a first direction, and a second elongate portion 750b with a major axis extending along soft tissue support 710 in a second direction different from the first direction. As shown in FIG. 12C, elongate portion 750a has opposed convex edges, and elongate portion 750b has a convex edge and a concave edge. It will be understood, however, that one or both of elongate portions 750a and 750b may have concave and/or convex edges, as desired for the intended use of soft tissue implant 700. Elongate portions 750a and 750b may be formed as flat, planar pieces or having a three-dimensional contour, e.g., in a sling or banana shape. As with other soft tissue grafts, soft tissue graft portions 750a and 750b can be configured to maintain their respective two- or three-dimensional shapes.

Figure 12D:
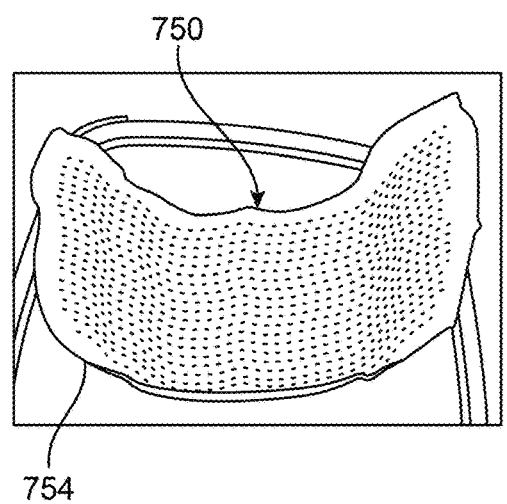

In the example shown in FIG. 12D, soft tissue graft 750 has a contour as described above with respect to the soft tissue graft of FIG. 12A. Soft tissue graft 750 of FIG. 12D is meshed to include small apertures than the soft tissue graft 750 of FIG. 12A, in order to increase strength and stability of the soft tissue graft 750.

Each example of soft tissue graft 750 is meshed to form a number of apertures 758. Apertures 758 may extend all of the way through soft tissue graft 750, or may extend only part of the way through soft tissue graft 750. Apertures 758 may each have the same shape and size, or may have different shapes and sizes. Apertures 758 may be linear, or may include a multi-directional separation or cut in surface 752. Possible shapes for the multi-directional separation include S-shapes, Z-shapes, J-shapes, L-shapes, X-shapes, omega shapes, or mirror images thereof.

The positioning and density of apertures 758 on soft tissue graft 750 may be uniform across surface 752, or may vary. In some examples, no apertures are positioned within a predetermined distance from peripheral edge 754, in order to create a zone for steady and secure suturing of soft tissue graft 750 during implantation.

Figure 13A:
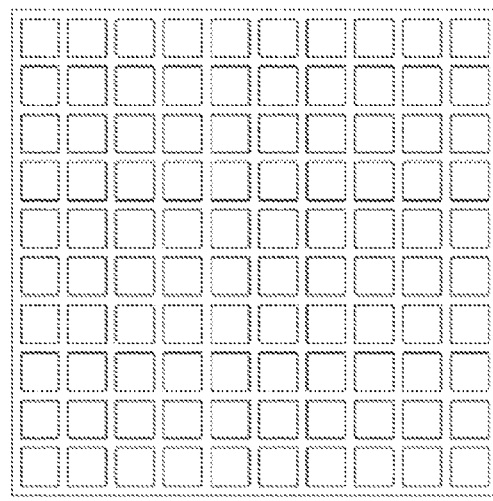
FIGS. 13A-13F are diagrams showing example configurations of the soft tissue grafts of FIGS. 12A-12D and/or example configurations of synthetic mesh materials.
Figure 13B:
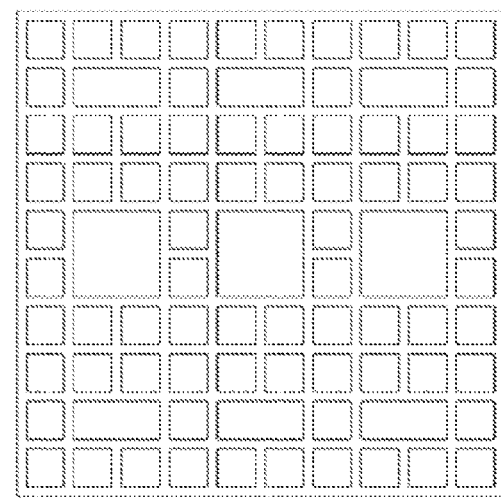
Figure 13C:
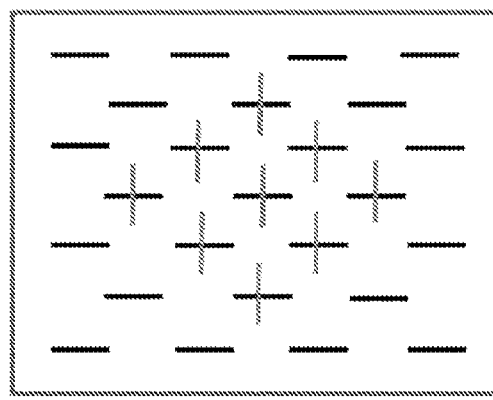
Figure 13D:
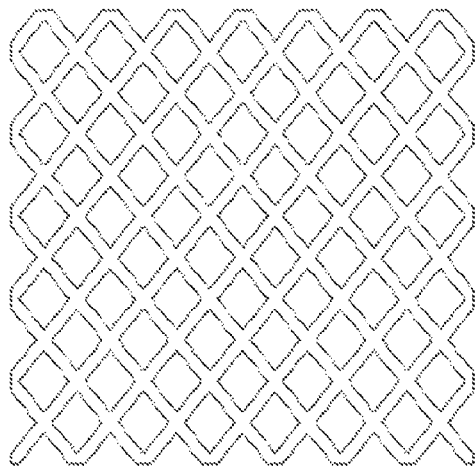
Figure 13E:
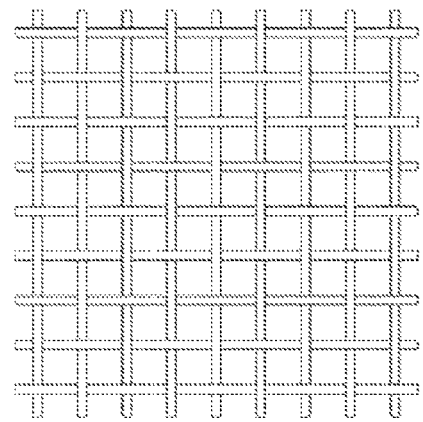
Figure 13F:
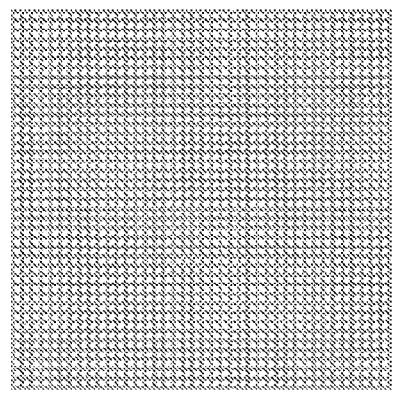
Figure 14A:
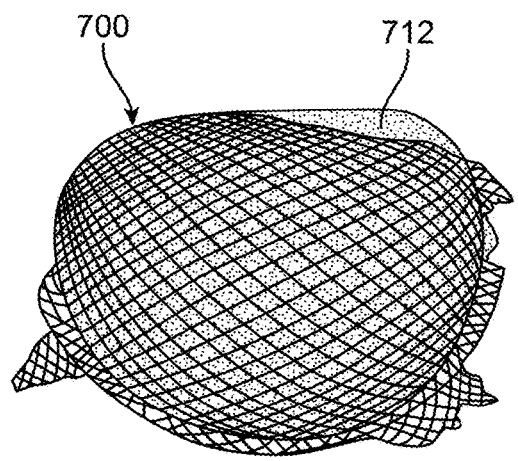
FIGS. 14A-14D show examples of a soft tissue implant incorporating the soft tissue graft of FIG. 12A.
Figure 14B:
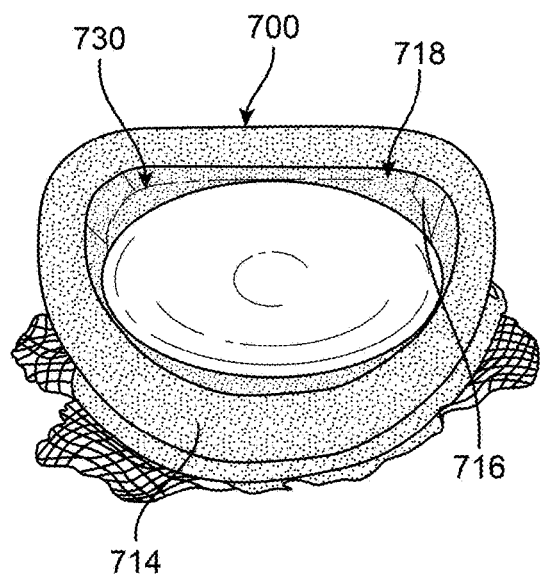
Figure 14C:
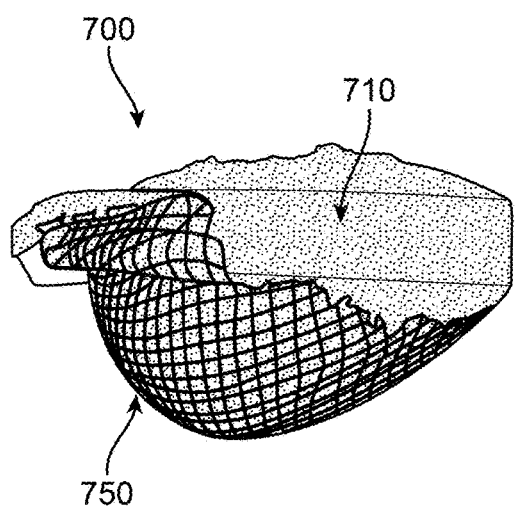
Figure 14D:
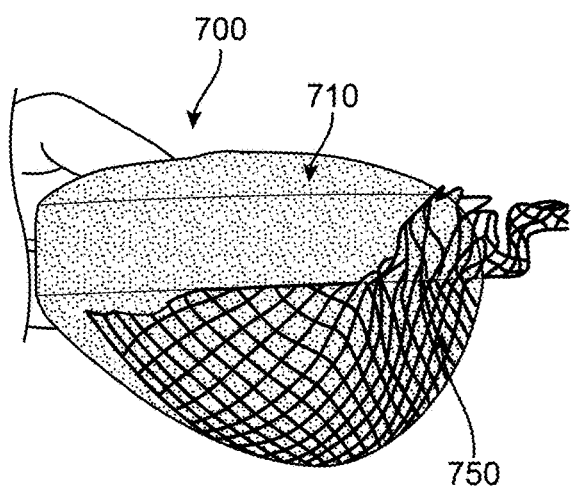
Figure 15A:
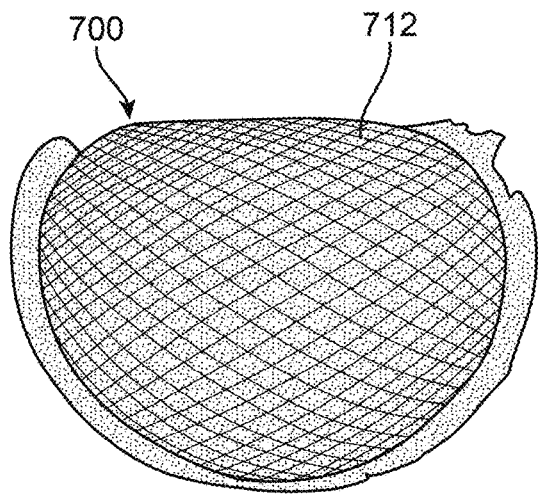
FIGS. 15A-15D show examples of another soft tissue implant incorporating the soft tissue graft of FIG. 12A.
Figure 15B:
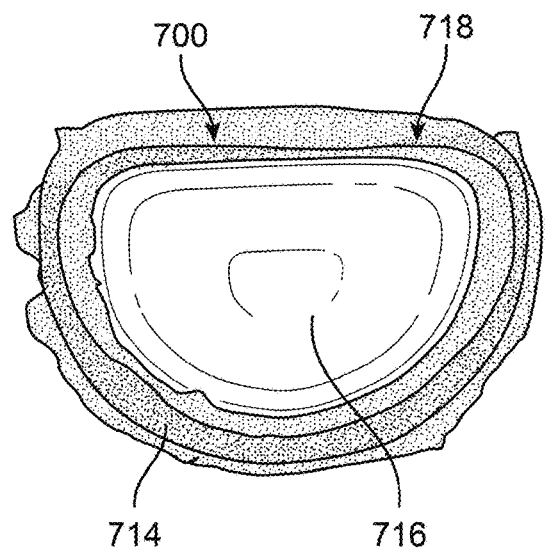
Figure 15C:
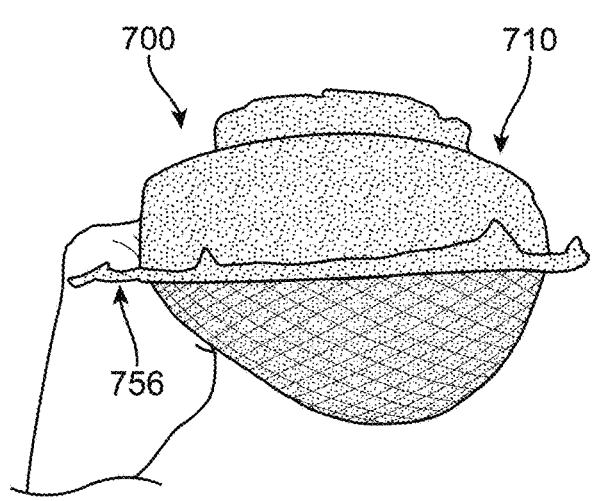
Figure 15D:
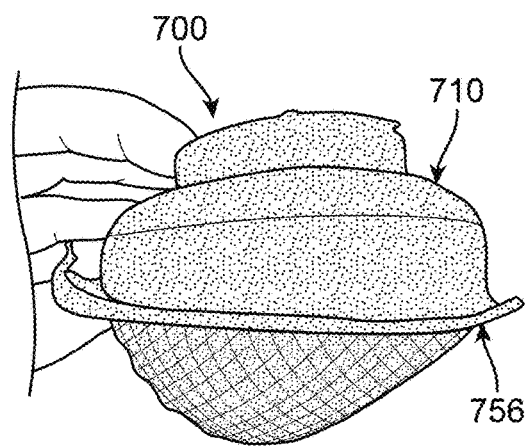
Figure 16A:
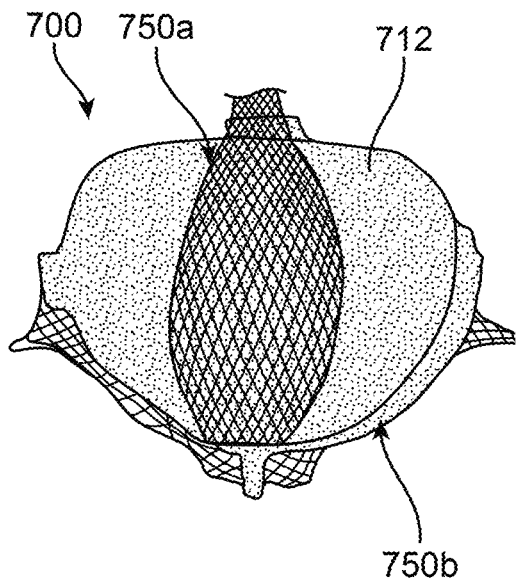
FIGS. 16A-16D show examples of a soft tissue implant incorporating the soft tissue graft of FIG. 12C.
Figure 16B:
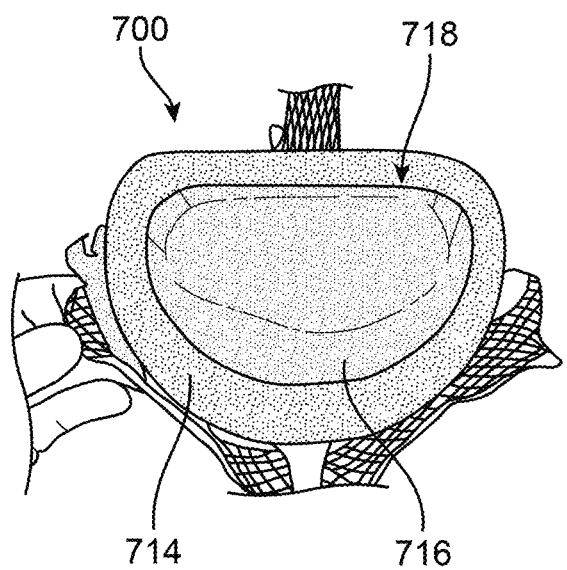
Figure 16C:
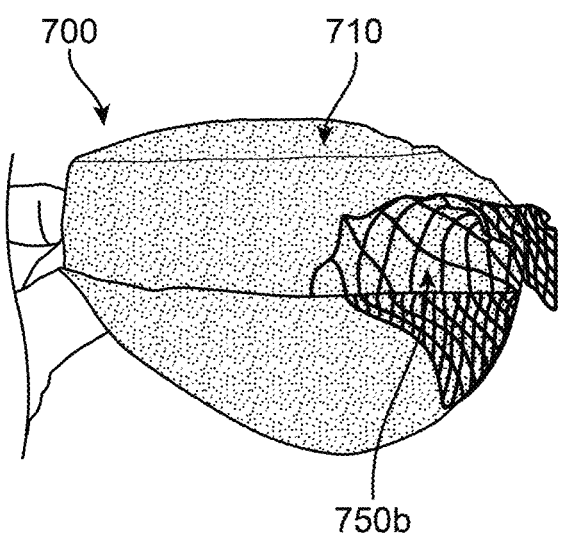
Figure 16D:
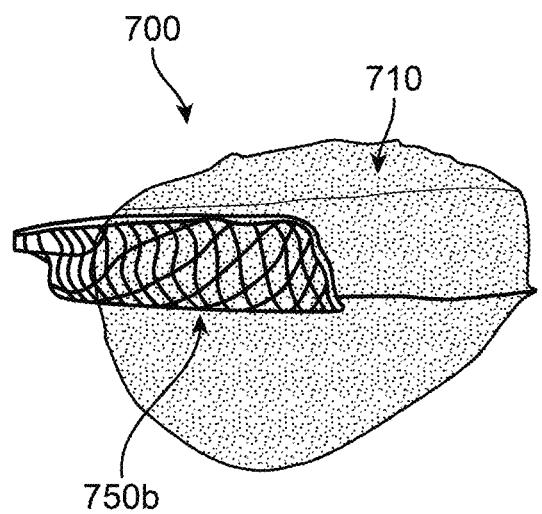
Figure 17A:
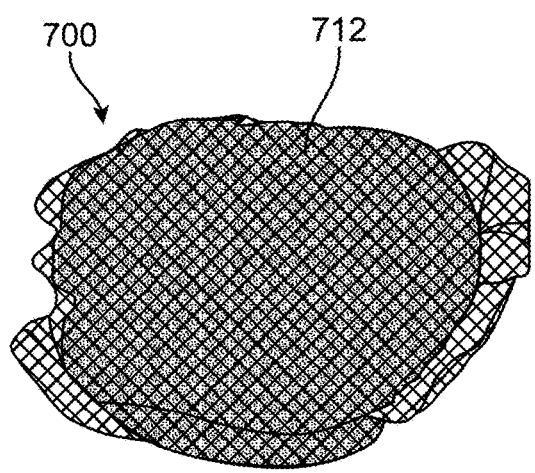
FIGS. 17A-17D show examples of a soft tissue implant incorporating a synthetic material.
Figure 17B:
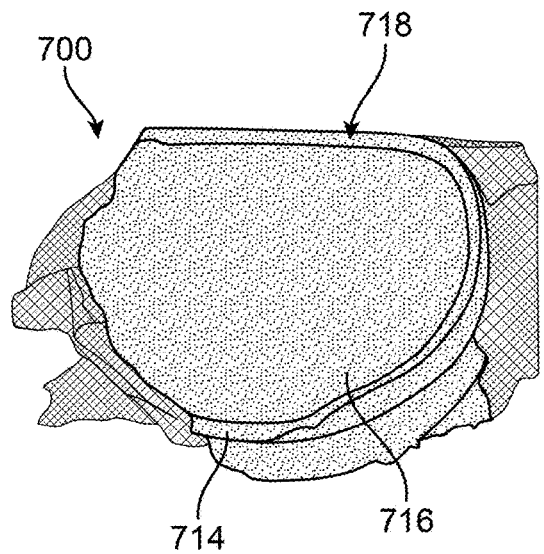
Figure 17C:
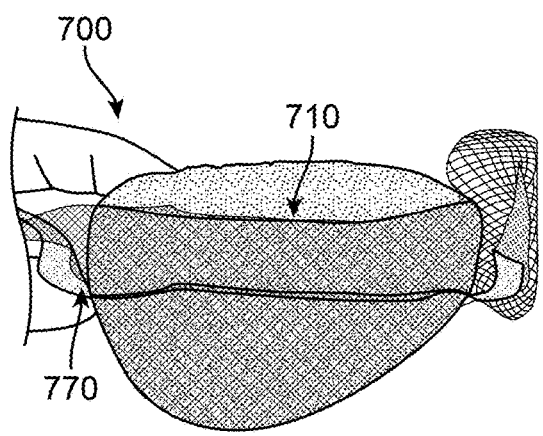
Figure 17D:
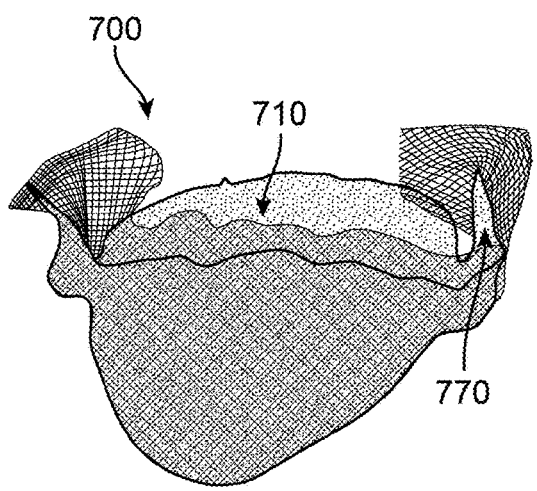

FIGS. 13A to 13F illustrate examples of different aperture layouts of soft tissue graft 750, or alternatively, of a synthetic mesh material. As shown in FIG. 13A, soft tissue graft 750 or synthetic mesh material may be meshed in a uniform, symmetrical pattern in which all apertures have a common size and shape, for example, a square shape. As shown in FIG. 13B, soft tissue graft 750 or synthetic mesh material may be meshed in a pattern which includes apertures of different sizes, in order to promote stretching and coverage in predetermined directions. As shown in FIG. 13C, soft tissue graft 750 or synthetic mesh material may be meshed in a pattern having slits in one direction in a peripheral area of the graft and having slits in 2 perpendicular directions in a central area. This perpendicular slits can provide elongation at both directions. As shown in FIG. 13D, soft tissue graft 750 or synthetic mesh material may be meshed in a uniform, symmetrical pattern in which all apertures have a common size and shape, for example, a diamond shape. As shown in FIG. 13E, the apertures of soft tissue graft 750 or synthetic mesh material may be formed by weaving strips or strands of tissue material, for example, in a basket weave pattern. FIG. 13F depicts an example configuration of a synthetic mesh material, discussed in greater detail below.

In one example, apertures 758 are all of substantially the same size, e.g., within a size variation from an average aperture size of 10% or less. An average length of apertures 758 may be from 0.3, 0.4, 0.5, 0.6, 0.7 or 0.8, 2, 4, 6 or 8 mm to 10, 20, 25, 28, 30, 35 or 40 mm. Apertures 758 may all have a length in a range of from 1 mm to 10 mm. Adjacent apertures 758 may be spaced apart at a distance of from 0.5 mm to 30 mm. The aperture length and spacing may be selected such that the ratio of average distance between adjacent apertures to average length of apertures is from 0.5, 0.6, 0.7, 0.8, 0.9, 0.95, or 0.99 or more and/or less than 1.0, 0.99, 0.95, 0.9, 0.8, 0.7, or 0.6. In some examples, this ratio may be from 0.2 to 0.99, from 0.3 to 0.9, from 0.5 to 0.8, or from 0.6 to 0.8.

Alternative or additionally, apertures 758 may be characterized by the area created by the aperture with or without stretching of the processed tissue material of soft tissue graft. When the aperture is formed by cutting the tissue material without removing any part of the tissue material, the size of the aperture is zero prior to any stretching of the processed tissue material. When the aperture is formed by removing tissue material, the aperture may have an area even without stretching of the processed tissue material.

The size and/or density of apertures 758 may be adjusted to control for the strength of soft tissue graft 750. It will be understood that larger and/or denser apertures may mean less soft tissue material is needed to form soft tissue graft 750 (since more stretching of the soft tissue will be possible), but smaller or less denser apertures may be used to preserve the strength of soft tissue graft 750. An average area of apertures 758 formed in tissue material of soft tissue graft 750 may be from 0, 0.1, 0.4, 0.5, 1, 5, 8 or 10 mm$^2$ to 50, 100, 150, 180 or 200 mm$^2$. Apertures 758 may all have an area in a range of from 0.5 mm$^2$ to 200 mm$^2$.

The density of apertures 758 in the meshed soft tissue graft 750 may be 100, 80, 60, 40, 20, 10, 5 or 2 apertures/cm$^2$ of the tissue material or more, and 200, 150, 90, 70, 50, 30, 10 or 5 apertures/cm$^2$ of the tissue material or less. The density of apertures 758 in the meshed soft tissue graft 750 may also be from 2 to 200, from 5 to 10, from 10 to 100, from 1 to 300, from 15 to 150, from 15 to 40, or from 20 to 70 apertures/cm$^2$ of the tissue material. In some examples, soft tissue graft 750 has a plurality of apertures that form from 1, 5, 10, 15, 20, 25, 30, 35, 40, 45, 50, 55, 60, 65 or 70% to 35, 40, 45, 50, 55, 60, 65, 70, 75, 80, 85, 90 or 95% opening area based on the total area of soft tissue graft 750. Apertures 758 may form from 4% to 98%, 10% to 80%, 30% to 70%, 40% to 60%, or 48% to 54% opening area based on the total area of the soft tissue graft 750.

The meshed tissue material may include a plurality of linear apertures arranged in closely spaced rows and/or columns. In one example, linear apertures may be arranged in rows extending along a length of the soft tissue graft. This arrangement may promote elongation of soft tissue graft 750 in a width direction of soft tissue graft 750, while limiting elongation of processed tissue material in a length direction of soft tissue graft 750, when compared to a non-meshed soft tissue graft.

As shown in FIGS. 14A-14D, soft tissue graft 750 may be positioned along and/or adhered to anterior surface 712 of soft tissue support 710. Alternatively, as shown in FIGS. 15A-15D, a soft tissue graft may be embedded within soft tissue support 710 between anterior surface 712 and posterior surface 714. As shown in FIGS. 16A-16D, soft tissue graft 750a may extend from an upper edge to a lower edge of anterior surface 712, while soft tissue graft 750b extends along the lower edge of anterior surface 712, in order to form a cradle for soft tissue implant 700 during implantation.

In some examples, soft tissue graft 750 can be cut in such a way that allows for a suturing zone or zones on the periphery of the graft without adversely impacting the biomechanical strength of the graft, and without impacting the placement of apertures in the soft tissue. The final soft tissue grafts allow for intra-operative suturing at an edge of the graft, while eliminating risk of pull-out of sutures through apertures in the graft. In some examples, soft tissue graft 750 may be formed with no apertures positioned within a predetermined distance from edges of the soft tissue graft 750.

In some examples, soft tissue graft 750 may be formed with a plurality of suture tabs distributed around peripheral edge 754. Suture tabs may be provided to enable soft tissue graft 750 to be sutured directly to the musculature and/or subcutaneous tissue of the subject during implantation, in order to support soft tissue support 710 and breast implant 730 without the need to directly suture or adhere soft tissue support 710 or breast implant 730 to the musculature during implantation.

Soft tissue graft 750 comprises tissue material which has been processed to be suitable for implantation. Such processing may include cleaning the tissue material, disinfecting the tissue material, skiving the tissue material to a predetermined thickness, removing cellular elements and small molecular weight solutes from the tissue material (i.e. "decellularizing" the tissue material), plasticizing the tissue material, packaging the tissue material, and/or sterilizing the tissue material. During plasticization, the internal matrix of the tissue material may be impregnated with one or more plasticizers. Tissue material may further be frozen and/or freeze-dried to promote stability and storage.

The tissue material for forming soft tissue graft 750 may not be dispersed, but may be formed from a uniform piece of soft tissue. As such, soft tissue graft 750 may be stronger and denser than the dispersed porous soft tissue material of soft tissue support 710.

Meshing of soft tissue graft 750 may be performed by cutting through the processed tissue material with a suitable tool or apparatus such as a mesher. For example, a meshed soft tissue graft may be prepared by using a cutting die that has border blades to cut the outside border rim matching the shape of the blades, a blade-free area that renders a suture zone around or adjacent peripheral edge 754, and blades in the center area to cut through and mesh the tissue material to form apertures 758.

In an alternative embodiment, meshed soft tissue graft 750 may be replaced with a synthetic mesh material 770 to form a soft tissue composite implant 700, as shown in FIGS. 17A-17D. Synthetic mesh material 770 may be any meshed material which is not formed exclusively from biological soft tissue, including polymer meshes or composite meshes including synthetic and biological materials. Synthetic mesh material 770 may provide a number of advantages over soft tissue graft 750, including for example easier shaping and contouring, simplified manufacturing of soft tissue implant 700, and larger sizing. In particular, the synthetic mesh material 770 may be prefabricated in the final shape of implant 700, prior to being joined with soft tissue support 710. Synthetic mesh material 770 may further be configured to hold its shape, such that synthetic mesh material 770 can be pre-contoured in a predetermined shape before or during manufacture of soft tissue implant 700.

Suitable materials for use as synthetic mesh material 770 will be known in the art and include permanent and absorbable synthetic material. Permanent synthetic material includes but is not limited to polypropylene (PP), polyester, or expanded polytetrafluoroethylene (ePTFE), lightweight PP, or a combination of these materials. Absorbable synthetic material includes but is not limited to absorbable materials such as DEXON™ and VICRYL™, polyglycolic acid, polyglycolide, trimethylene, and trimethylene carbonate, and/or a combination of these materials. Another group of synthetic material can be derived from natural sources including plants such as cellulose, hemicelluloses, lignin, and animal such as silk and hair/wool. As an example, synthetic mesh material 770 may be formed from any of the material disclosed in U.S. Pat. No. 10,532,127, the contents of which are incorporated herein by reference in their entirety.

In either embodiment, soft tissue graft 750 and/or synthetic mesh material 770 are provided to improve the biomechanical strength, and in particular the tensile strength, of soft tissue implant 700, relative to a version of soft tissue implant including an unsupported soft tissue support 710. In some examples, at least 50%, at least 60%, at least 70%, at least 80%, at least 90%, or at least 95% of a tensile strength of soft tissue implant 700 is provided by soft tissue graft 750 or synthetic mesh material 770.

Figure 18:
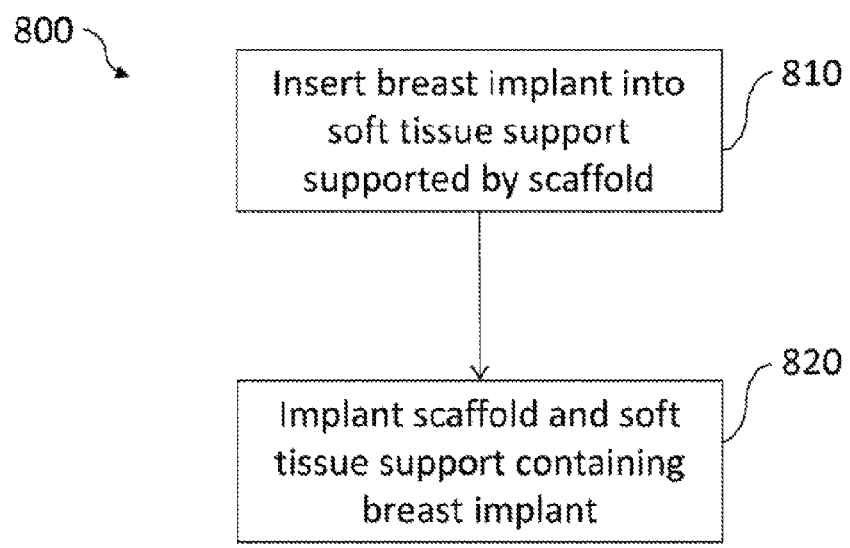
FIG. 18 is a flowchart illustrating an example of a method of use of a soft tissue implant.

FIG. 18 illustrates a method 800 of use of a soft tissue implant. The method includes inserting a breast implant into a soft tissue support supported by a scaffold (in step 810), and implanting the soft tissue support and scaffold (in step 820). Additional details are described below with respect to the elements of soft tissue implant 700.

In step 810, a breast implant is inserted into a soft tissue support. In an example, breast implant 730 is inserted into soft tissue support 710, a unitary piece of processed porous tissue material supported by a scaffold. The scaffold may take the form of soft tissue graft 750 and/or synthetic mesh material 770. In particular, breast implant 730 is inserted through opening 718 into cavity 716 defined by posterior surface 714 of soft tissue support 710.

In step 820, the soft tissue support is implanted. In an example, soft tissue support 710 containing breast implant 730 and supported by a scaffold (collectively, soft tissue implant 700) is implanted into the subject. In a preferred embodiment, soft tissue implant 700 is implanted in a sub-glandular insertion, in which soft tissue implant 700 is positioned in front of (anterior to) a musculature of the subject. In examples where the scaffold comprises soft tissue graft 750 including a suture zone or suture tabs, this step may include suturing soft tissue graft 750 to a musculature and/or subcutaneous tissue of a subject at the suture zone or suture tabs. In examples where the scaffold comprises synthetic mesh material 770, this step may include suturing portions of synthetic mesh material 770 to a musculature and/or subcutaneous tissue of a subject. In other embodiments, soft tissue implant 700 can be implanted by other processes, including post-pectoral muscle implant, prepectoral muscle implant, two-stage complete submuscular placement (with the use of a tissue expander), single-stage implant breast reconstruction, and/or single-stage direct to implant.

Step 820 may further include implanting soft tissue implant 700 so that opening 718 of soft tissue support 710 faces the musculature and/or subcutaneous tissue of the subject. Such a position may expose breast implant 730 to the musculature and/or subcutaneous tissue, such that at least a portion of breast implant 730 contacts the musculature and/or subcutaneous tissue of the subject through opening 718, promoting post-implantation adhesion and support of soft tissue implant 700. Alternatively or additionally, soft tissue implant 700 may be implanted including an inferior dermal flap, or with a dermal graft, in order to improve stability and adherence during or after implantation.

Method 800 may optionally include a step, before the inserting step, of supporting the soft tissue support with the scaffold. In an example, soft tissue support 710 is supported with soft tissue graft 750 and/or with synthetic mesh material 770. As part of this step, soft tissue graft 750 and/or synthetic mesh material 770 may be positioned covering at least a portion of the anterior surface 712 of soft tissue support 710. In some examples, this step may include stretching or reconfiguring soft tissue graft 750 and/or synthetic mesh material 770 to match the contour of soft tissue support 710. In other examples, synthetic mesh material 770 may be pre-contoured in the desired shape of soft tissue support 710. This supporting step may further include suturing or otherwise adhering soft tissue graft 750 and/or synthetic mesh material 770 to soft tissue support 710.

Figure 19:
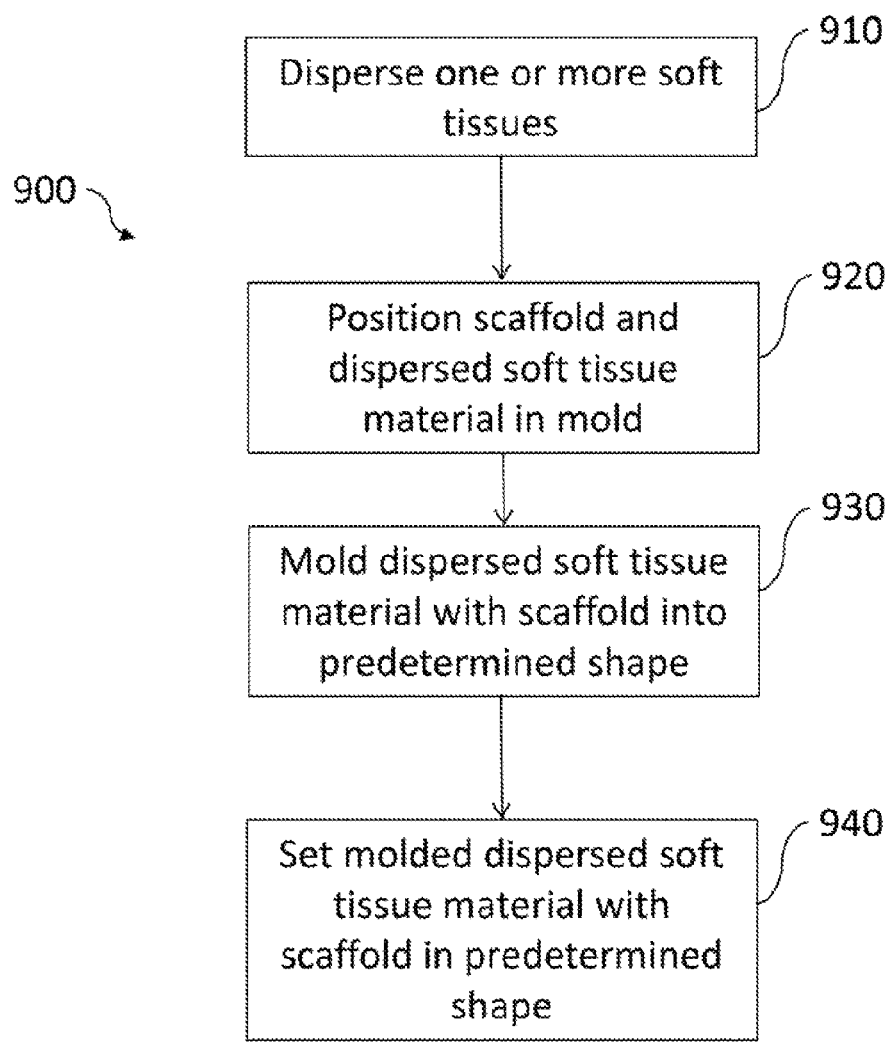
FIG. 19 is a flowchart illustrating an example of a method of making a soft tissue implant.

FIG. 19 illustrates a method 900 of making a soft tissue implant. The method includes dispersing one or more soft tissues, positioning a scaffold, molding the dispersed soft tissue material with the scaffold, and setting the molded dispersed soft tissue material with the scaffold. Additional details are described below with respect to the elements of soft tissue implant 700.

In step 910, one or more soft tissues are dispersed. In an example, soft tissue material is dispersed to create dispersed soft tissue material. The soft tissue material may be dispersed by any of the processes disclosed herein, or by any other known process. In some examples, a non-naturally occurring crosslinker and a non-naturally occurring carrier are not added to the dispersed soft tissue material. The dispersed soft tissue material may be dispersing in a solution or solvent, so that the dispersed soft tissue material is suitable for pouring, injecting, spreading, molding, or other manipulation.

Figure 20B:
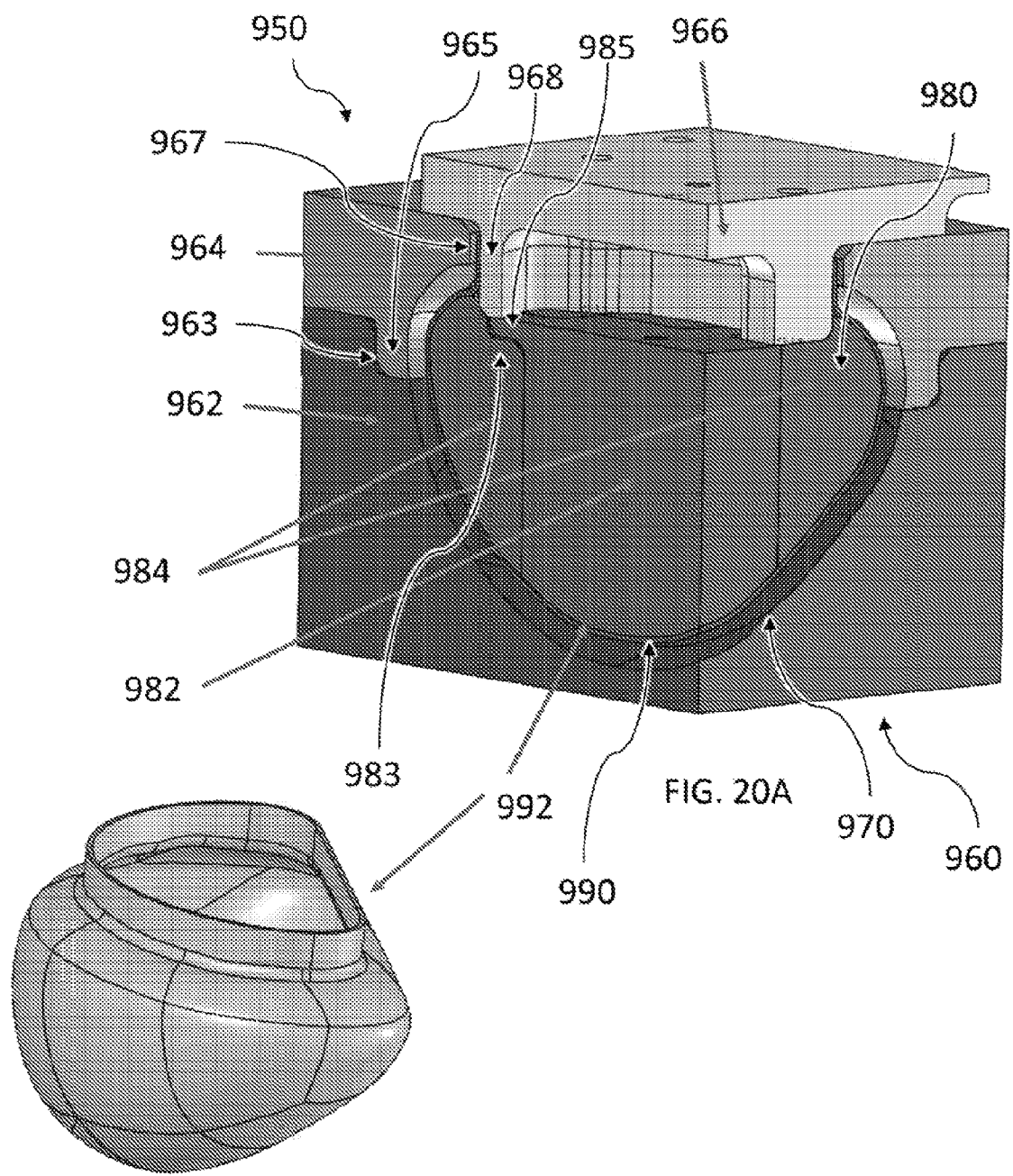

In step 920, a scaffold and the dispersed soft tissue material are positioned in a mold. An example of a mold 950 for molding the shape of soft tissue support 710 with the scaffold is shown in FIGS. 20A and 20B in one quarter cross-section. As shown in FIG. 20A, mold 950 includes an outer mold section 960 and an inner mold section 980. Outer mold section 960 and/or inner mold section 980 may be formed from suitable polymer materials including, for example, polyetherimide (PEI) or acrylonitrile butadiene styrene (ABS).

As shown in FIG. 20A, outer mold section 960 may be formed from multiple separable components, including a base component 962, an upper component 964, and a mold top component 966. In one example, base component 962 defines a bore 963 configured to receive a protrusion 965 formed on upper component 964, in order to align upper component 964 with base component 962. Likewise, upper component 964 defines a bore 967 configured to receive a protrusion 968 formed on top component 966, in order to align top component 966 with upper component 964. Outer mold section 960 defines an outer surface 970 for molding anterior surface 712 of soft tissue support 710. Outer surface 970 may have a spheroid or ellipsoid shape corresponding to a desired shape of soft tissue implant 700.

As shown in FIG. 20A, inner mold section 980 may be formed from multiple separable components, including a central component 982 and one or more peripheral components 984, in order to facilitate removal of inner mold section 980 from outer mold section 960 after molding of soft tissue implant 700. In one example, peripheral component(s) 984 define a bore 983 configured to receive a protrusion 985 formed on central component 982, in order to align central component 982 with peripheral component(s) 984. Inner mold section 980 defines an inner surface 990 for molding the posterior surface 714, including cavity 716, of soft tissue support 710. Inner surface 990 may have a spheroid or ellipsoid shape corresponding to a desired shape of soft tissue implant 700. The shape of inner mold section 980 may be selected to correspond to the shape of outer mold section 960, in order to form a soft tissue support having a uniform thickness. Alternatively, the shape of inner mold section 980 may be selected to create a varying thickness of the soft tissue support.

Inner mold section 980 may further include a mold liner 992, as shown in FIG. 20B, for lining and defining outer surface 990. Mold liner 992 may be provided to facilitate a uniform shape and texture for posterior surface 714, and/or to facilitate easy removal of soft tissue implant 700 from mold 950. Suitable materials for use as mold liner 992 include, for example, silicone.

Figure 21A:
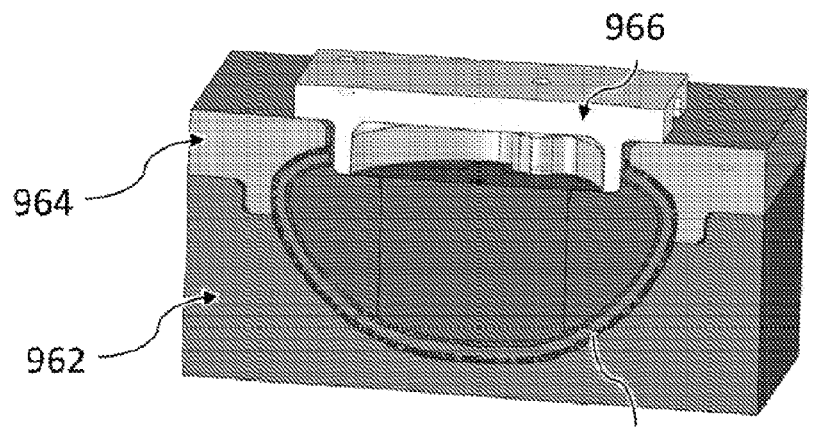
FIGS. 21A-21C show examples of steps of a molding processes for manufacturing a soft tissue implant using the mold of FIG. 20A.
Figure 21B:
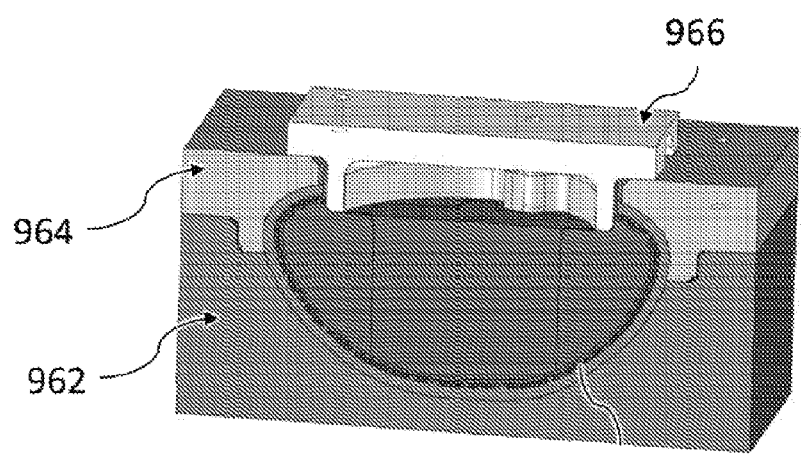
Figure 21C:
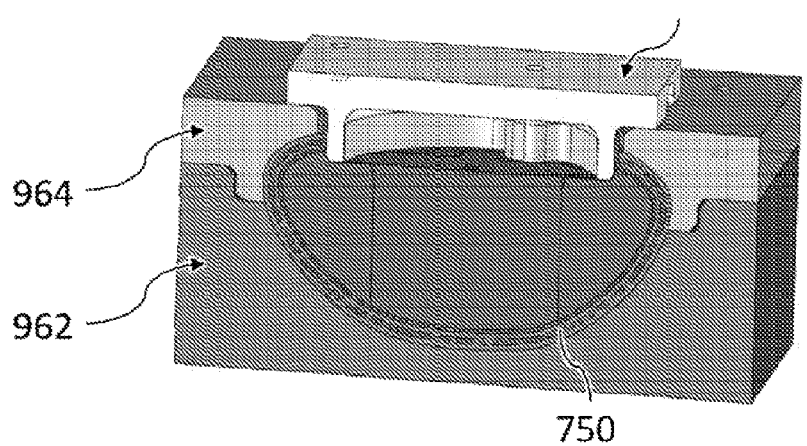

Outer surface 970, inner surface 990, and/or mold liner 992, may be configured as smooth surfaces, or may include predetermined textures or patterns. Smooth mold surfaces may simplify molding and release of soft tissue supports and implants. Conversely, textured mold surfaces increase surface area of the soft tissue supports and implants, and may thereby promote angiogenesis and tissue ingrowth following implantation, thereby speeding the post-implantation healing process The scaffold may take the form of soft tissue graft 750 and/or synthetic mesh material 770. In either embodiment, the scaffold is positioned in base component 962 of mold 950 based on the desired position of the scaffold relative to soft tissue support 710 in soft tissue implant 700. In one example shown in FIG. 21A, soft tissue graft 750 and/or synthetic mesh material 770 may be positioned against outer surface 970 such that, in the finally molded and set soft tissue implant 700, soft tissue graft 750 and/or synthetic mesh material 770 will be positioned on the anterior surface 712 of soft tissue support 710. In another example shown in FIG. 21B, soft tissue graft 750 and/or synthetic mesh material 770 may be positioned against inner surface 990 such that, in the finally molded and set soft tissue implant 700, soft tissue graft 750 and/or synthetic mesh material 770 will be positioned on posterior surface 714 of soft tissue support 710. In another example shown in FIG. 21C, soft tissue graft 750 and/or synthetic mesh material 770 may be suspended between outer surface 970 and inner surface 990 so that, in the finally molded and set soft tissue implant 700, soft tissue graft 750 and/or synthetic mesh material 770 is embedded within soft tissue support 710. The dispersed soft tissue material may be inserted (e.g., poured or injected) into mold 950 following the positioning of the scaffold.

In step 930, the dispersed soft tissue material with the scaffold is molded into a predetermined shape for the soft tissue implant. In an example, the dispersed soft tissue material is molded into the shape of soft tissue support 710, namely, a unitary piece of material having an anterior surface 712 and a posterior surface 714 defining a cavity 716 sized to receive a breast implant therein.

In the preceding step, the dispersed soft tissue material may be inserted (e.g., poured or injected) into base component 962. To mold the dispersed soft tissue material, upper component 964, top component 966, and inner mold section 980 are inserted into the dispersed soft tissue material in base component 962 in order to define the inner surface 990 of mold 950, and press the dispersed soft tissue material against the outer surface 970 of mold 950.

During molding, mold components may be affixed to one another, e.g., by screws or other fasteners. For example, upper component 964 may be affixed to base component 961, mold top component may be affixed to upper component 965, and/or inner mold section 980 may be affixed to mold top component 966.

In step 940, the shape of the molded dispersed soft tissue material with the scaffold is set in the desired shape, to produce a soft tissue implant. In an example, the molded dispersed soft tissue material is frozen and/or freeze-dried and/or plasticized by any of the processes disclosed herein, or by any other known process. This step sets the shape of the molded dispersed soft tissue material, resulting in a processed porous tissue material having a shape and structure suitable for use as soft tissue support 710. The scaffold is adhered or affixed in place during the setting of the tissue material.

The desired shape of the scaffold may also be set during the setting of the dispersed soft tissue material in step 240. Alternatively, method 900 may include a step of pre-contouring the scaffold (such as synthetic mesh material 770) before positioning the scaffold in mold 950. Performing a step of pre-contouring synthetic mesh material 770 prior to positioning, molding, or setting may help facilitate reliable positioning and shaping of synthetic mesh material 770.

After the shape of the soft tissue material is set to form soft tissue support 710, the inner mold section 980 is removed from cavity 716. In one example, mold top component 966 is removed, followed by central component 982 of inner mold section 980, followed by peripheral components 984 of inner mold section 980.

In some embodiments of soft tissue implant 700, breast implant 730 is entirely surrounded or encapsulated by soft tissue support 710, such soft tissue support 710 lacks any opening 718 for insertion or removal of breast implant 730. To manufacture such soft tissue implants, method 900 may further include steps of positioning a breast implant in the mold, and molding the dispersed soft tissue material around the breast implant with the mold. In an example, breast implant 730 is inserted into mold 950 and suspended in place within mold 950. The dispersed soft tissue material with the scaffold is then molded into a predetermined shape surrounding breast implant 730, such that breast implant 730 is completely surrounded or encapsulated by the dispersed soft tissue material.

The above description of molding soft tissue implant 700 is provided for the purpose of illustrating one manufacturing possibility. Other manufacturing processes for forming the disclosed soft tissue supports, grafts, and implants described herein will be apparent from the disclosure. Further examples are identified below for the purposes of illustration.

In addition to pouring the dispersed soft tissue material into a mold, the soft tissue supports and/or implants may be formed using injection molding or blow molding. The soft tissue supports and/or implants may be formed using compression molding (with or without a sandwich assembly), extrusion molding, vacuum-assisted molding, centrifugal molding or casting. The soft tissue supports and/or implants may be formed by spraying or coating the dispersed soft tissue material into an internal shape or mold, spraying or coating the material onto a tissue or synthetic scaffold and into an internal shape or mold, spraying or coating the material onto a tissue or synthetic scaffold and onto an external shape (e.g., a mandrel or core), spraying or coating the material onto an external shape (e.g., a mandrel or core), spraying or coating the material onto a flat surface, and/or spraying or coating the material onto a tissue or synthetic scaffold and onto a flat surface. The soft tissue supports and/or implants may be formed by forming the material into a shape without a mold, forming the material into an internal shape with a mold, or forming the material onto an external shape (e.g., a mandrel or core). The soft tissue supports and/or implants may be formed by placing synthetic or tissue "fibers" into an internal shape such as a mold, compression molding along with synthetic or tissue "fibers," spraying or coating the material onto a tissue or synthetic fiber grid and onto an external shape (e.g., a mandrel or core), spraying or coating the material onto a tissue or synthetic scaffold and onto a flat surface, and/or adding fibers in a random, or systematic pattern to a surface or internal matrix of soft tissue material. The soft tissue supports and/or implants may be formed using extrusion molding to for tube structures, along with adding fibers in a random, or systematic pattern; by spraying or coating the material onto an external shape (e.g., a mandrel or core) and adding fibers in a random or systematic pattern to the internal or external surface; and/or by molding the material onto an external cylinder shape (e.g., a mandrel or core) and adding fibers in a random or systematic pattern to the internal or external surface. The soft tissue supports and/or implants may be formed by a deep drawing process, in which a blank is radially drawn into a forming die by the mechanical action of a punch. The soft tissue supports and/or implants may be formed using 3-D printing technology to computer guide the deposits of dispersed soft tissue material into a predetermined shape, or a patient specific shape. The soft tissue supports and/or implants may be formed using saws, mills, or other removal processes to convert a generic, or starter shape into a predetermined shape, or a patient specific shape. The soft tissue supports and/or implants may be formed using dispersed soft tissue material to create a fiber or fibers, and weaving or knitting the fibers into sheets or structures (e.g., with a loom). Other manufacturing processes for forming the disclosed soft tissue supports, grafts, and implants will be apparent from the description above.

Figure 22A:
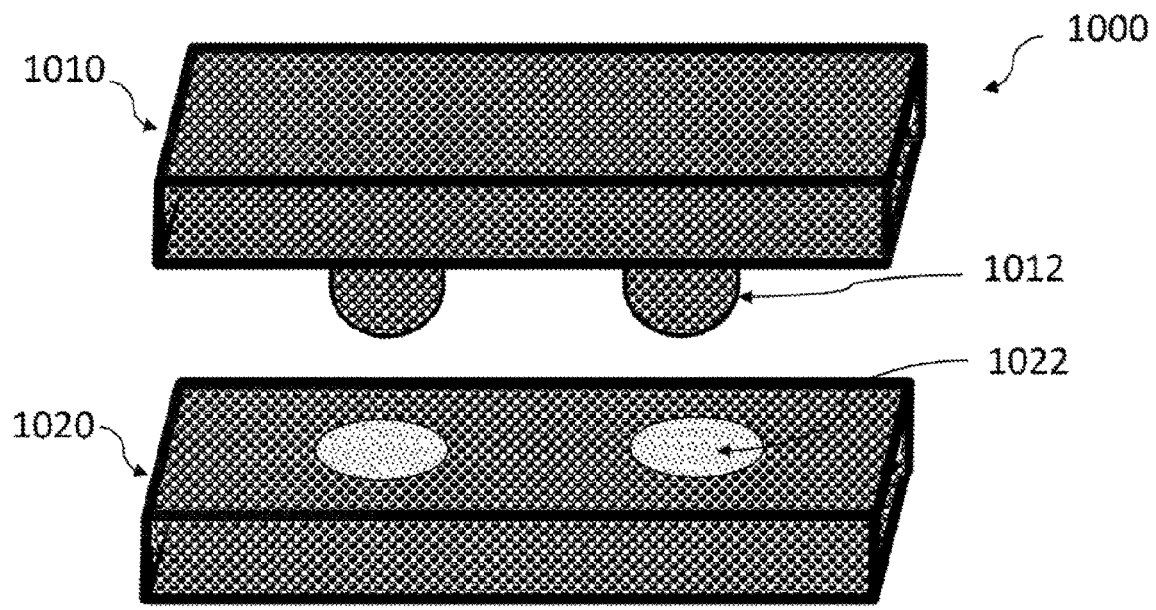
FIGS. 22A and 22B show examples of another soft tissue implant.
Figure 22B:
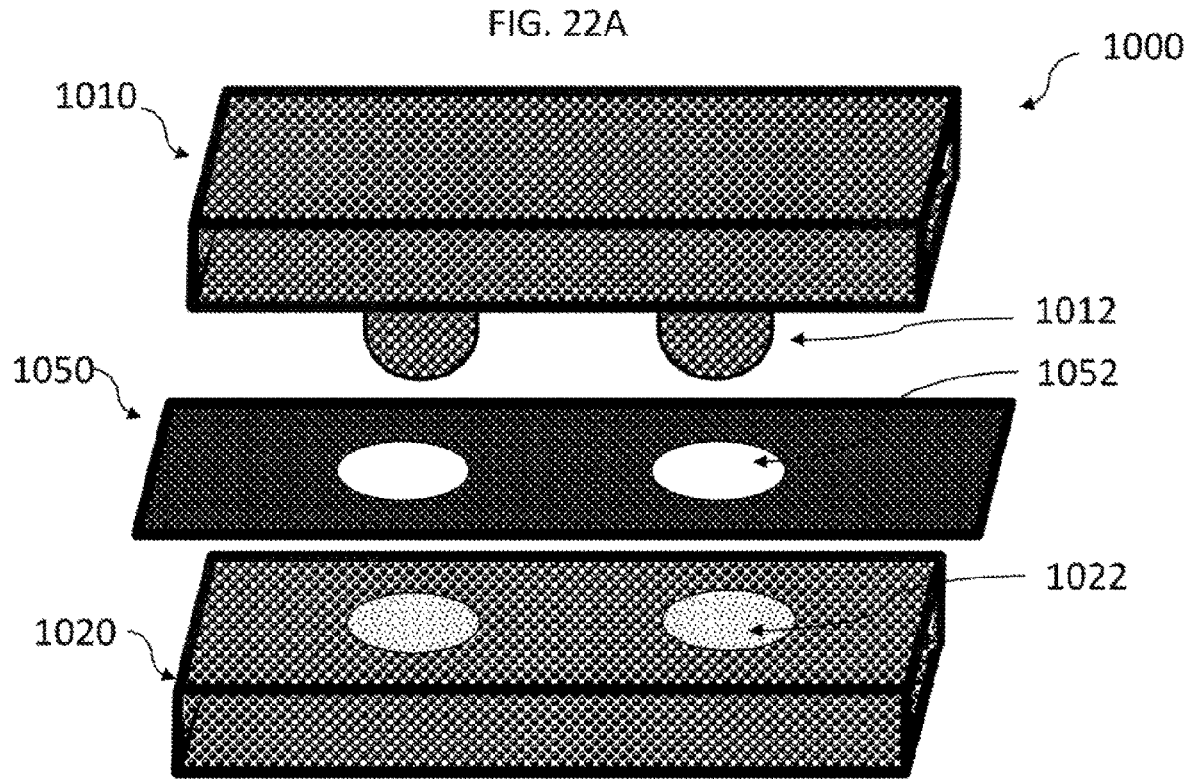

FIGS. 22A and 22B illustrate components of another example soft tissue implant 1000. Generally, soft tissue implant 1000 includes plural soft tissue supports 1010 and 1020. Soft tissue implant 1000 may further include a soft tissue graft 1050. Soft tissue implant 1000 may include any of the features, structures, configurations, and/or characteristics described above with respect to soft tissue implant 700. In particular, soft tissue supports 1010 and 1020 may be formed as described above with respect to soft tissue support 710, and soft tissue graft 1050 may be formed as described above with respect to soft tissue graft 750. Alternatively, soft tissue graft 750 may be replaced with a material as described above with respect to synthetic mesh material 770. Additional details regarding soft tissue implant 1000 are set forth below.

As shown in FIG. 22A, soft tissue implant 1000 can be formed from multiple discrete soft tissue supports 1010 and 1020. While two soft tissue supports 1010 and 1020 are shown to form soft tissue implant 1000, it will be understood that soft tissue implant 1000 may be formed from any number of discrete soft tissue supports, as desired for the particular application and/or use of soft tissue implant 1000.

Soft tissue supports 1010 and 1020 may have the same or different material properties. For example, soft tissue supports 1010 and 1020 may be the same or different in biological material, weight, density, hydration, size, shape, elasticity, biomechanical strength, or other material properties. Based on their desired properties, soft tissue supports 1010 and 1020 may be manufactured together (e.g., within a common mold with or without a dividing element), or may be manufactured separately from different dispersions of soft tissue material. To form corresponding mating structures, it may be desired to use one previously manufactured soft tissue support as a portion of a mold to manufacture a corresponding soft tissue support.

Each soft tissue support 1010 and 1020 has a respective mating structure 1012 and 1022. The mating structures 1012 and 1022 are configured to mate with one another, so that soft tissue supports 1010 and 1020 can combine to form the structure and shape of soft tissue implant 1000 prior to or during implantation. Soft tissue supports 1010 and 1020 may include interlocking structures to prevent soft tissue supports 1010 and 1020 from separating prior to, during, or following implantation. Further, soft tissue supports 1010 and 1020 may be configured to create a friction fit during assembly to prevent soft tissue supports 1010 and 1020 from separating prior to, during, or following implantation. Still further, soft tissue supports 1010 and 1020 may be sutured together prior to or during implantation to prevent soft tissue supports 1010 and 1020 from separating.

In an example, mating structure 1012 comprises one or more projections formed on a surface of soft tissue support 1010, and mating structure 1022 comprises one or more corresponding indentations formed on a surface of soft tissue support 1022. Other shapes, sizes, or structures for forming mating structures 1012 and 1022 will be appreciated from the disclosure.

Soft tissue implant 1000 is not limited to being formed from discrete soft tissue supports. As shown in FIG. 22B soft tissue implant 1000 may further include a soft tissue graft 1050. While a single unitary soft tissue graft 1050 is shown, it will be understood that soft tissue implant 1000 may be formed from any number of discrete soft tissue grafts, as desired for the particular application and/or use of soft tissue implant 1000.

Soft tissue graft 1050 may have one or more mating structures 1052. Mating structure 1052 may be configured to mate with one or both of mating structures 1012 and/or 1022 of soft tissue supports 1010 and 1020 prior to or during implantation.

In an example, mating structure 1052 comprises one or more apertures form in soft tissue graft 1050 which are sized to engage with projections of mating structure(s) 1012. Other shapes, sizes, or structures for forming mating structure 1050 will be appreciated from the disclosure. In this example, soft tissue graft 1050 is configured to be held in place between soft tissue supports 1010 and 1020 during assembly of soft tissue implant 1000.

Alternatively, soft tissue graft 1050 may omit a mating structure, and may be adhered to one of soft tissue supports 1010 and 1020 during manufacture of the soft tissue support 1010, e.g., during the setting of the dispersed soft tissue material of soft tissue support 1010 and/or soft tissue support 1020.

As shown in FIG. 22B, soft tissue graft 1050 may be formed larger (e.g. in a width and or length direction) than the soft tissue supports 1010 and 1020 on either side thereof. With this structure, the protruding portions of soft tissue graft 1050 may be used for suturing during implantation.

Figure 23A:
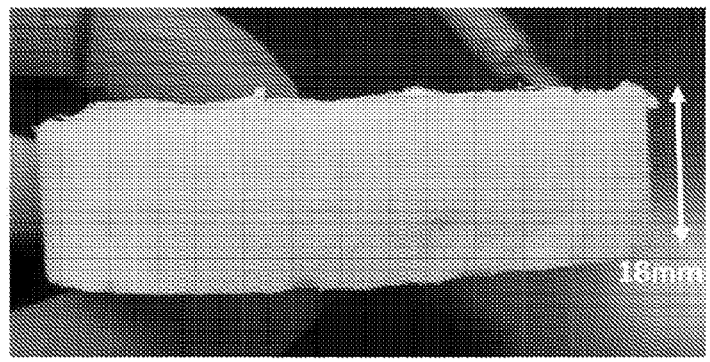
FIGS. 23A-23C show examples of a soft tissue support before (A) and after (B) compression, and after hydration (C).
Figure 23B:
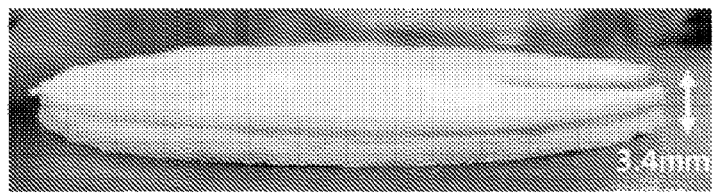
Figure 23C:
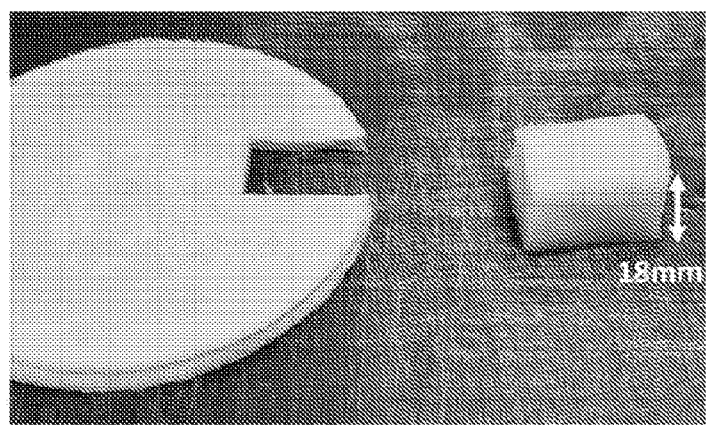

Example images of a prototype soft tissue support according to the disclosure herein are illustrated in FIGS. 23A-23C. As shown in FIG. 23A, the soft tissue support may have a thickness of about 18 mm in a dry state, e.g., following manufacturing, setting, and/or dehydration of the soft tissue support. As shown in FIG. 23B, the soft tissue support may have a thickness of about 3.4 mm in a compressed state, e.g., following compressing of the soft tissue support of FIG. 23A with a 15 ton hydraulic press. Such compression may be performed during or simultaneously with dehydration of the soft tissue support. To illustrate the ability of the soft tissue support to reform following rehydration, a small rectangular piece is cut out from the soft tissue support and rehydrated (e.g., with isotonic saline) in FIG. 23C. As shown in FIG. 23C, the soft tissue support may be capable of elastically returning to its original thickness of around 18 mm.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A soft tissue support comprising:
a unitary piece of processed porous tissue material having an anterior portion and a posterior portion, the anterior and posterior portions defining a cavity therebetween, the cavity sized to receive a breast implant therein, the cavity having at least one opening sized to receive the breast implant therethrough, wherein the at least one opening is provided at a periphery of the processed porous tissue material between the anterior portion and the posterior portion.

2. The soft tissue support of claim 1, wherein the processed porous tissue material comprises a dispersed soft tissue material.

3. The soft tissue support of claim 2, wherein the dispersed soft tissue material has been frozen, freeze-dried, and/or plasticized.

4. The soft tissue support of claim 2, wherein the dispersed soft tissue material lacks both a non-naturally occurring crosslinker and a non-naturally occurring carrier.

5. The soft tissue support of claim 2, wherein the dispersed soft tissue material is molded to form the anterior and posterior portions defining the cavity.

6. The soft tissue support of claim 1, wherein the anterior portion has a thickness which is less than a thickness of the posterior portion.

7. The soft tissue support of claim 1, wherein the anterior and posterior portion each have an upper portion and a lower portion, the respective upper portions having a thickness which is greater than a thickness of the respective lower portions.

8. The soft tissue support of claim 1, wherein the anterior and posterior portions have a shape which is at least partially curved.

9. The soft tissue support of claim 8, wherein the shape of the anterior and posterior portions is round or elliptical.

10. The soft tissue support of claim 1, wherein the cavity has a shape which is at least partially curved.

11. The soft tissue support of claim 10, wherein the shape of the cavity is round or elliptical.

12. The soft tissue support of claim 1, wherein the cavity has a volume of from 40 to 100 cubic centimeters.

13. A soft tissue support comprising:
a unitary piece of processed porous tissue material having an anterior portion and a posterior portion, the anterior and posterior portions defining a cavity therebetween, the cavity sized to receive a breast implant therein, the cavity having at least one opening sized to receive the breast implant therethrough, wherein the at least one opening is provided in the posterior portion.

14. The soft tissue support of claim 13, wherein the processed porous tissue material comprises a dispersed soft tissue material.

15. The soft tissue support of claim 14, wherein the dispersed soft tissue material has been frozen, freeze-dried, and/or plasticized.

16. The soft tissue support of claim 14, wherein the dispersed soft tissue material lacks both a non-naturally occurring crosslinker and a non-naturally occurring carrier.

17. The soft tissue support of claim 14, wherein the dispersed soft tissue material is molded to form the anterior and posterior portions defining the cavity.

18. The soft tissue support of claim 13, wherein the anterior portion has a thickness which is less than a thickness of the posterior portion.

19. The soft tissue support of claim 13, wherein the anterior and posterior portion each have an upper portion and a lower portion, the respective upper portions having a thickness which is greater than a thickness of the respective lower portions.

20. The soft tissue support of claim 13, wherein the anterior and posterior portions have a shape which is at least partially curved.

21. The soft tissue support of claim 20, wherein the shape of the anterior and posterior portions is round or elliptical.

22. The soft tissue support of claim 13, wherein the cavity has a shape which is at least partially curved.

23. The soft tissue support of claim 22, wherein the shape of the cavity is round or elliptical.

24. The soft tissue support of claim 13, wherein the cavity has a volume of from 40 to 100 cubic centimeters.

25. A soft tissue support comprising:
a unitary piece of processed porous tissue material having an anterior portion and a posterior portion, the anterior and posterior portions defining a cavity therebetween, the cavity sized to receive a breast implant therein, the cavity having at least one opening sized to receive the breast implant therethrough, wherein the at least one opening has a cross-sectional area less than a cross-sectional area of the cavity.

26. The soft tissue support of claim 25, wherein the processed porous tissue material comprises a dispersed soft tissue material.

27. The soft tissue support of claim 26, wherein the dispersed soft tissue material has been frozen, freeze-dried, and/or plasticized.

28. The soft tissue support of claim 26, wherein the dispersed soft tissue material lacks both a non-naturally occurring crosslinker and a non-naturally occurring carrier.

29. The soft tissue support of claim 26, wherein the dispersed soft tissue material is molded to form the anterior and posterior portions defining the cavity.

30. The soft tissue support of claim 25, wherein the anterior portion has a thickness which is less than a thickness of the posterior portion.

31. The soft tissue support of claim 25, wherein the anterior and posterior portion each have an upper portion and a lower portion, the respective upper portions having a thickness which is greater than a thickness of the respective lower portions.

32. The soft tissue support of claim 25, wherein the anterior and posterior portions have a shape which is at least partially curved.

33. The soft tissue support of claim 32, wherein the shape of the anterior and posterior portions is round or elliptical.

34. The soft tissue support of claim 25, wherein the cavity has a shape which is at least partially curved.

35. The soft tissue support of claim 34, wherein the shape of the cavity is round or elliptical.

36. The soft tissue support of claim 25, wherein the cavity has a volume of from 40 to 100 cubic centimeters.

37. A soft tissue support comprising:
a unitary piece of processed porous tissue material having an anterior portion and a posterior portion, the anterior and posterior portions defining a cavity therebetween, the cavity sized to receive a breast implant therein, the cavity having at least one opening sized to receive the breast implant therethrough, wherein the cavity comprises a plurality of openings.

38. The soft tissue support of claim 37, wherein the plurality of openings are distributed around a periphery of the processed porous tissue material between the anterior portion and the posterior portion.

39. The soft tissue support of claim 37, wherein the processed porous tissue material comprises a dispersed soft tissue material.

40. The soft tissue support of claim 39, wherein the dispersed soft tissue material has been frozen, freeze-dried, and/or plasticized.

41. The soft tissue support of claim 39, wherein the dispersed soft tissue material lacks both a non-naturally occurring crosslinker and a non-naturally occurring carrier.

42. The soft tissue support of claim 39, wherein the dispersed soft tissue material is molded to form the anterior and posterior portions defining the cavity.

43. The soft tissue support of claim 37, wherein the anterior portion has a thickness which is less than a thickness of the posterior portion.

44. The soft tissue support of claim 37, wherein the anterior and posterior portion each have an upper portion and a lower portion, the respective upper portions having a thickness which is greater than a thickness of the respective lower portions.

45. The soft tissue support of claim 37, wherein the anterior and posterior portions have a shape which is at least partially curved.

46. The soft tissue support of claim 45, wherein the shape of the anterior and posterior portions is round or elliptical.

47. The soft tissue support of claim 37, wherein the cavity has a shape which is at least partially curved.

48. The soft tissue support of claim 47, wherein the shape of the cavity is round or elliptical.

49. The soft tissue support of claim 37, wherein the cavity has a volume of from 40 to 100 cubic centimeters.

50. A soft tissue implant comprising:
a unitary piece of processed porous tissue material having an anterior portion and a posterior portion, the anterior and posterior portions defining a cavity therebetween, the cavity having an opening; and
a breast implant positioned within the cavity,
and further comprising:
a soft tissue graft configured to support the processed porous tissue material and the breast implant.

51. The soft tissue implant of claim 50, wherein the soft tissue graft is positioned to cover the opening of the cavity.

52. The soft tissue implant of claim 50, wherein the soft tissue graft has a contour which follows at least a portion of a contour of the anterior portion of the processed porous tissue material.

53. The soft tissue implant of claim 50, wherein the soft tissue graft comprises one or more apertures extending therethrough.

54. A soft tissue implant comprising:
a unitary piece of processed porous tissue material defining a cavity sized to receive a breast implant therein; and
a synthetic mesh material configured to support the processed porous tissue,
wherein at least than 60% of a tensile strength of the soft tissue implant is provided by the synthetic mesh material,
wherein the cavity is defined at least in part by a posterior surface of the processed porous tissue material, and the synthetic mesh material is positioned along an anterior surface of the processed porous tissue material opposite the posterior surface of the processed porous tissue material.

55. The soft tissue implant of claim 54, wherein the processed porous tissue material comprises a dispersed soft tissue material.

56. The soft tissue implant of claim 55, wherein the dispersed soft tissue material has been frozen, freeze-dried, and/or plasticized.

57. The soft tissue implant of claim 55, wherein the dispersed soft tissue material lacks both a non-naturally occurring crosslinker and a non-naturally occurring carrier.

58. The soft tissue implant of claim 54, wherein the processed porous tissue material has a shape which is at least partially curved.

59. The soft tissue implant of claim 58, wherein the dispersed soft tissue material is molded to form the at least partially curved shape.

60. The soft tissue implant of claim 54, wherein the soft tissue graft has a contour which follows at least a portion of a contour of the processed porous tissue material.

61. The soft tissue implant of claim 54, wherein the soft tissue graft has at least a partially spherical or ellipsoidal contour.

62. The soft tissue implant of claim 54, further comprising the breast implant positioned within the cavity.

63. A soft tissue implant comprising:
a unitary piece of processed porous tissue material defining a cavity sized to receive a breast implant therein; and
a synthetic mesh material configured to support the processed porous tissue,
wherein at least than 60% of a tensile strength of the soft tissue implant is provided by the synthetic mesh material,
wherein the cavity is defined at least in part by a posterior surface of the processed porous tissue material, and the synthetic mesh material is positioned along the posterior surface of the processed porous tissue material.

64. The soft tissue implant of claim 63, wherein the processed porous tissue material comprises a dispersed soft tissue material.

65. The soft tissue implant of claim 64, wherein the dispersed soft tissue material has been frozen, freeze-dried, and/or plasticized.

66. The soft tissue implant of claim 64, wherein the dispersed soft tissue material lacks both a non-naturally occurring crosslinker and a non-naturally occurring carrier.

67. The soft tissue implant of claim 63, wherein the processed porous tissue material has a shape which is at least partially curved.

68. The soft tissue implant of claim 67, wherein the dispersed soft tissue material is molded to form the at least partially curved shape.

69. The soft tissue implant of claim 63, wherein the soft tissue graft has a contour which follows at least a portion of a contour of the processed porous tissue material.

70. The soft tissue implant of claim 63, wherein the soft tissue graft has at least a partially spherical or ellipsoidal contour.

71. The soft tissue implant of claim 63, further comprising the breast implant positioned within the cavity.

72. A soft tissue implant comprising:
a unitary piece of processed porous tissue material defining a cavity sized to receive a breast implant therein; and
a synthetic mesh material configured to support the processed porous tissue,
wherein at least than 60% of a tensile strength of the soft tissue implant is provided by the synthetic mesh material,
wherein the cavity is defined at least in part by a posterior surface of the processed porous tissue material, and the synthetic mesh material is embedded between the posterior surface of the processed porous tissue material and an anterior surface of the processed porous tissue material opposite the posterior surface of the processed porous tissue material.

73. The soft tissue implant of claim 72, wherein the processed porous tissue material comprises a dispersed soft tissue material.

74. The soft tissue implant of claim 73, wherein the dispersed soft tissue material has been frozen, freeze-dried, and/or plasticized.

75. The soft tissue implant of claim 73, wherein the dispersed soft tissue material lacks both a non-naturally occurring crosslinker and a non-naturally occurring carrier.

76. The soft tissue implant of claim 72, wherein the processed porous tissue material has a shape which is at least partially curved.

77. The soft tissue implant of claim 76, wherein the dispersed soft tissue material is molded to form the at least partially curved shape.

78. The soft tissue implant of claim 72, wherein the soft tissue graft has a contour which follows at least a portion of a contour of the processed porous tissue material.

79. The soft tissue implant of claim 72, wherein the soft tissue graft has at least a partially spherical or ellipsoidal contour.

80. The soft tissue implant of claim 72, further comprising the breast implant positioned within the cavity.

\* \* \* \* \*

UNITED STATES PATENT AND TRADEMARK OFFICE
CERTIFICATE OF CORRECTION

PATENT NO. : 12,285,328 B2
APPLICATION NO. : 17/440522
DATED : April 29, 2025
INVENTOR(S) : Xiaofei Qin et al.

Page 1 of 1

It is certified that error appears in the above-identified patent and that said Letters Patent is hereby corrected as shown below:

In the Claims

At Claim 54, Column 43, Line 41, "at least than 60% of a tensile strength" should read --at least 60% of a tensile strength--

At Claim 63, Column 44, Line 12, "at least than 60% of a tensile strength" should read --at least 60% of a tensile strength--

At Claim 72, Column 44, Line 49, "at least than 60% of a tensile strength" should read --at least 60% of a tensile strength--

Signed and Sealed this
Twenty-eighth Day of October, 2025

John A. Squires
*Director of the United States Patent and Trademark Office*